(12) United States Patent
Fearnot et al.

(10) Patent No.: US 12,319,904 B2
(45) Date of Patent: Jun. 3, 2025

(54) CELL TISSUE PROCESSING APPARATUS, SYSTEMS, METHODS, AND PRODUCTS

(71) Applicants: Cook Medical Technologies LLC, Bloomington, IN (US); Muffin Incorporated, West Lafayette, IN (US)

(72) Inventors: Neal Fearnot, West Lafayette, IN (US); Sarah Robbins, Lafayette, IN (US); Marc Buhrmester, Dayton, IN (US); Joshua Krieger, Topsfield, MA (US); Gabriel Converse, Lafayette, IN (US)

(73) Assignees: Cook Medical Technologies LLC, Bloomington, IN (US); Muffin Incorporated, West Lafayette, IN (US)

( * ) Notice: Subject to any disclaimer, the term of this patent is extended or adjusted under 35 U.S.C. 154(b) by 810 days.

(21) Appl. No.: 17/310,261

(22) PCT Filed: Jan. 28, 2020

(86) PCT No.: PCT/US2020/015284
§ 371 (c)(1),
(2) Date: Jul. 27, 2021

(87) PCT Pub. No.: WO2020/159899
PCT Pub. Date: Aug. 6, 2020

(65) Prior Publication Data
US 2022/0177824 A1    Jun. 9, 2022

Related U.S. Application Data

(60) Provisional application No. 62/797,409, filed on Jan. 28, 2019.

(51) Int. Cl.
*B01L 3/00*      (2006.01)
*B01F 23/00*     (2022.01)
(Continued)

(52) U.S. Cl.
CPC ............ *C12M 23/50* (2013.01); *C12M 23/46* (2013.01); *C12M 33/12* (2013.01); *C12M 35/04* (2013.01); *C12M 45/02* (2013.01)

(58) Field of Classification Search
CPC ...... C12M 23/50; C12M 23/46; C12M 33/12; C12M 35/04; C12M 45/02; C12M 21/08
See application file for complete search history.

(56) References Cited

U.S. PATENT DOCUMENTS

2014/0024112 A1    1/2014 Galiano et al.

FOREIGN PATENT DOCUMENTS

| WO | 0017317 A1 | 3/2000 |
| WO | 2009147482 A2 | 10/2009 |

(Continued)

OTHER PUBLICATIONS

International Search Report and Written Opinion, Application No. PCT/US2020/015284, dated Aug. 4, 2020.

(Continued)

*Primary Examiner* — Jennifer Wecker
*Assistant Examiner* — Oyeleye Alexader Alabi
(74) *Attorney, Agent, or Firm* — MacMillan, Sobanski & Todd, LLC

(57) ABSTRACT

Material processing apparatus, systems, methods, and products are described. An example of a material processing apparatus includes a holding member, a base, a tensioning member, an actuator, and a first inner member. The holding member defines a holding member passageway. The base is attached to the holding member. The tensioning member is partially disposed within the holding member passageway. The tensioning member defines a tensioning member passageway. The tensioning member is moveable relative to the holding member between a first position and a second position. The actuator is attached to the tensioning member (Continued)

and is moveable in a first direction and a second direction. Movement of the actuator results in movement of the tensioning member between its first position and second position. The first inner member is adapted to be disposed within the tensioning member passageway.

21 Claims, 25 Drawing Sheets

(51) Int. Cl.
| | |
|---|---|
| *B01F 23/41* | (2022.01) |
| *B01F 101/23* | (2022.01) |
| *B23Q 17/24* | (2006.01) |
| *C07K 14/705* | (2006.01) |
| *C12M 1/00* | (2006.01) |
| *C12M 1/26* | (2006.01) |
| *C12M 1/33* | (2006.01) |
| *C12M 1/34* | (2006.01) |
| *C12M 1/42* | (2006.01) |
| *C12M 3/00* | (2006.01) |
| *C12Q 1/04* | (2006.01) |
| *C12Q 1/18* | (2006.01) |
| *C12Q 1/686* | (2018.01) |
| *G01N 21/3577* | (2014.01) |
| *G01N 21/359* | (2014.01) |
| *G01N 21/39* | (2006.01) |
| *G01N 21/45* | (2006.01) |
| *G01N 21/64* | (2006.01) |
| *G01N 21/77* | (2006.01) |
| *G01N 21/78* | (2006.01) |
| *G01N 27/414* | (2006.01) |
| *G01N 27/62* | (2021.01) |
| *G01N 30/12* | (2006.01) |
| *G01N 30/68* | (2006.01) |
| *G01N 30/70* | (2006.01) |
| *G01N 30/72* | (2006.01) |
| *G01N 30/88* | (2006.01) |
| *G01N 33/00* | (2006.01) |
| *G01N 33/18* | (2006.01) |
| *G01N 33/50* | (2006.01) |
| *G01N 33/53* | (2006.01) |
| *G01N 33/543* | (2006.01) |
| *G01N 33/68* | (2006.01) |
| *G01N 33/74* | (2006.01) |
| *G01N 35/00* | (2006.01) |
| *G01N 35/10* | (2006.01) |
| *G06K 7/10* | (2006.01) |
| *G06K 7/14* | (2006.01) |
| *G06K 19/06* | (2006.01) |
| *G06K 19/07* | (2006.01) |
| *G06T 7/00* | (2017.01) |
| *G06T 7/90* | (2017.01) |
| *H01J 49/00* | (2006.01) |
| *H10K 10/46* | (2023.01) |
| *H10K 85/00* | (2023.01) |
| *H10K 85/20* | (2023.01) |

(56) References Cited

FOREIGN PATENT DOCUMENTS

| | | |
|---|---|---|
| WO | 2017198988 A2 | 11/2017 |
| WO | 2018149795 A1 | 8/2018 |

OTHER PUBLICATIONS

Australian Examination Report, Application No. 2020216912, dated Feb. 25, 2022.
Japanese Office Action, Application No. 2021544149, dated Dec. 12, 2023.
European Communication pursuant to Article 94(3) EPC, Application No. 20724245.4, dated Apr. 15, 2025.

CELL TISSUE PROCESSING APPARATUS, SYSTEMS, METHODS, AND PRODUCTS

CROSS-REFERENCE TO RELATED APPLICATION

This application claims the benefit of U.S. Provisional Application No. 62/797,409, filed Jan. 28, 2019. The entire disclosure of this related application is hereby incorporated by reference into this disclosure.

FIELD

The disclosure relates generally to the field of material processing for manufacturing and/or assembly environments. More particularly, the disclosure relates to material processing apparatus, systems, methods, and products. Specific examples described herein relate to passive tissue fixation useful in the manufacture of medical devices.

BACKGROUND

Generally, tissue fixation for medical products is utilized to preserve the properties of the tissue, such as mechanical properties, through cross-linking during chemical fixation, for example, and to render the tissue relatively inert for use in implantation. Currently, differential pressure processing systems are used to fix heart valves that include a tubular wall and valve leaflets. These systems allow fluid to flow through the tubular wall and past the valve during the fixation process, which presents significant drawbacks for processing other types of tissue. For example, current systems fail to provide a mechanism to maintain control of the forces exerted on the tissue over time. In addition, current systems fail to provide a mechanism for processing sheets of tissue and for attaching a sheet of tissue to the system without causing deformation during attachment. Highly distensible and low thickness tissues pose unique challenges related to attachment of the tissue to a system for processing. Specifically, due to the very low forces required to cause deformation of these tissues, large deformations can be imparted onto the tissue during attachment, which can impact the mechanical behavior of the tissue after processing. Tissues with highly consistent mechanical properties are desired for medical device manufacturing. Deformations imparted during attachment, uniform or not, can alter the internal stress and strain state and change the collagen configuration of the tissue during processing, often in an unpredictable or unknown manner, resulting in a less constituent material after processing.

Highly distensible and low thickness tissues pose additional challenges to traditional fixation systems and processes. For example, it is desired to impart a uniform and controllable stress and stain state greater than zero on these tissues during fixation and differential pressure techniques can be used to create such a state. However, due to leakage or diffusion of the fixation solution through the tissue during processing, the maintenance of a constant differential pressure is challenging in a passive fixation system. Furthermore, certain tissues that are desirable for chemical fixation (e.g., visceral pleura) are intimately attached to adjacent tissues, and the separation process often results in small holes in the tissue making the tissue unsuitable for differential pressure fixation in traditional passive fixation systems. Thus, an active system, typically incorporating pumps and pressure monitoring, is required to overcome these losses, which increases system complexity and cost.

Therefore, a need exists for new and useful material processing apparatus, systems, methods, and products.

SUMMARY OF SELECTED EXAMPLE EMBODIMENTS

Various material processing apparatus, systems, methods, and products are described herein.

An example material processing apparatus comprises a holding member, a base, a tensioning member, an actuator, and a first inner member. The holding member defines a holding member passageway that has an inside diameter. The base is attached to the holding member and defines a base passageway. The tensioning member is partially disposed within the holding member passageway. The tensioning member has an outside diameter and defines a tensioning member passageway. The tensioning member is moveable relative to the holding member between a first position and a second position. The outside diameter is less than the inside diameter of the holding member. The actuator is attached to the tensioning member and is moveable in a first direction and a second direction. Movement of the actuator results in movement of the tensioning member between its first position and second position. The first inner member is adapted to be disposed within the tensioning member passageway.

An example method of loading a sheet of tissue comprises: positioning a sheet of tissue on a loading member, a tensioning member, and an inner member such that a portion of the tissue is separated from the loading member, the tensioning member, and the inner member by a fluid layer disposed between the tissue and the loading member, the tensioning member, and the inner member; adjusting the position of the tissue; positioning a clamping member on the loading member; releasably attaching the clamping member to the loading member.

An example method of processing tissue comprises: positioning a material processing apparatus such that the first end of the loading member, the first end of the tensioning member, and the first end of the inner member are disposed on a first hypothetical plane; applying a fluid to the loading member, the tensioning member, and the first inner member; positioning a sheet of tissue on the loading member, the tensioning member, and the first inner member such that the tissue is in its resting state and a portion of the tissue is separated from the loading member, the tensioning member, and the first inner member by a fluid layer disposed between the tissue and the loading member, the tensioning member, and the first inner member; adjusting the position of the tissue; positioning a clamping member on the loading member; releasably attaching the clamping member to the loading member such that the tissue is in the clamped state; positioning the inner member such that the first end of the inner member is positioned on a second hypothetical plane that is disposed within the tensioning member passageway; positioning a material on the tissue such that the tissue sags and contacts the inner member; advancing the tensioning member to its second position; withdrawing the inner member from the tensioning member passageway; positioning the material processing apparatus in a bath of fluid for a period of time; removing the material processing apparatus from the bath of fluid; removing the clamping member from the loading member; removing the tissue from the loading member; placing the tissue in a fluid for a period of time.

Additional understanding of the example material processing apparatus, systems, methods, and products can be obtained by review of the detailed description, below, and the appended drawings.

DETAILED DESCRIPTION

The following detailed description and the appended drawings describe and illustrate various example embodiments of material processing apparatus, systems, methods, and products. The description and illustration of these examples are provided to enable one skilled in the art to make and use a material processing apparatus, a system, to practice a method of using a material processing apparatus, and to create a product. They are not intended to limit the scope of the claims in any manner.

Figure 14:
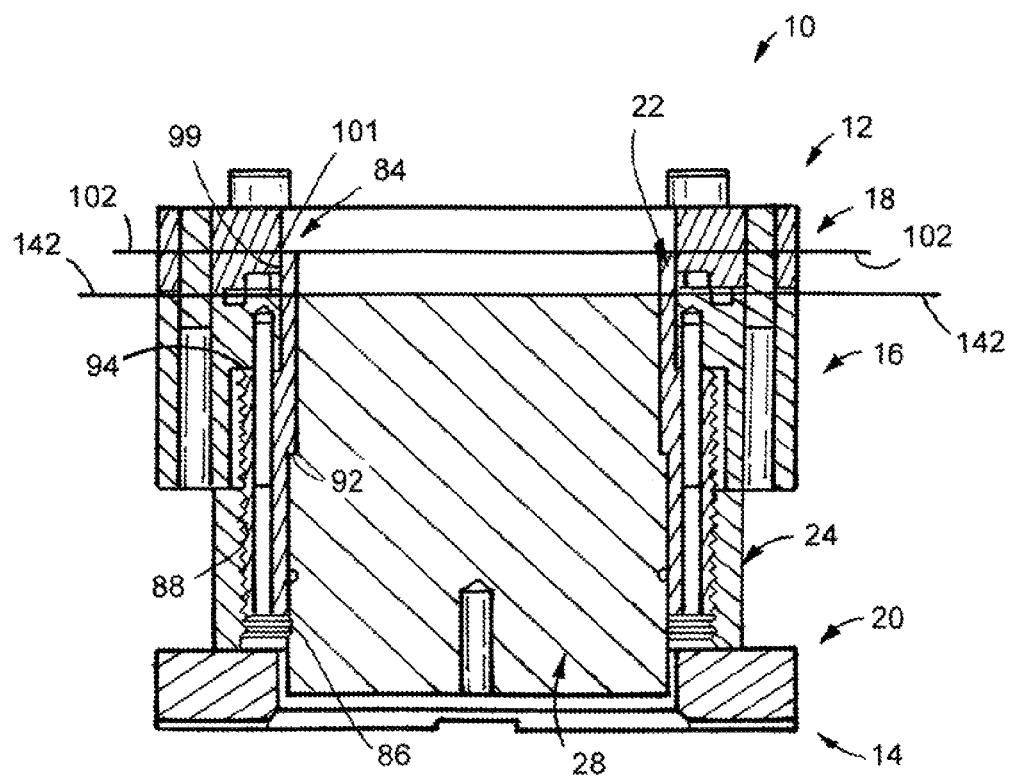
FIG. 14 is a cross-sectional view of the material processing apparatus illustrated in FIG. 2 taken along line 5-5. The material processing apparatus is in the tensioning configuration and includes a second inner member.

FIGS. 1, 2, 3, 4, 5, 6, 7, 8, 9, 10, 11, 12, 13, and 14 illustrate a first example material processing apparatus 10 that can be used to process tissue. The material processing apparatus 10 has a lengthwise axis 11, a first end 12, a second end 14, and includes a holding member 15, a base 20, a tensioning member 22, an actuator 24, a first inner member 26, and a second inner member 28. The material processing apparatus 10 is moveable between a loading configuration, as shown in FIGS. 1, 2, 3, 4, 5, 6, and 7, and a tensioning configuration, as shown in FIG. 14.

Figure 1:
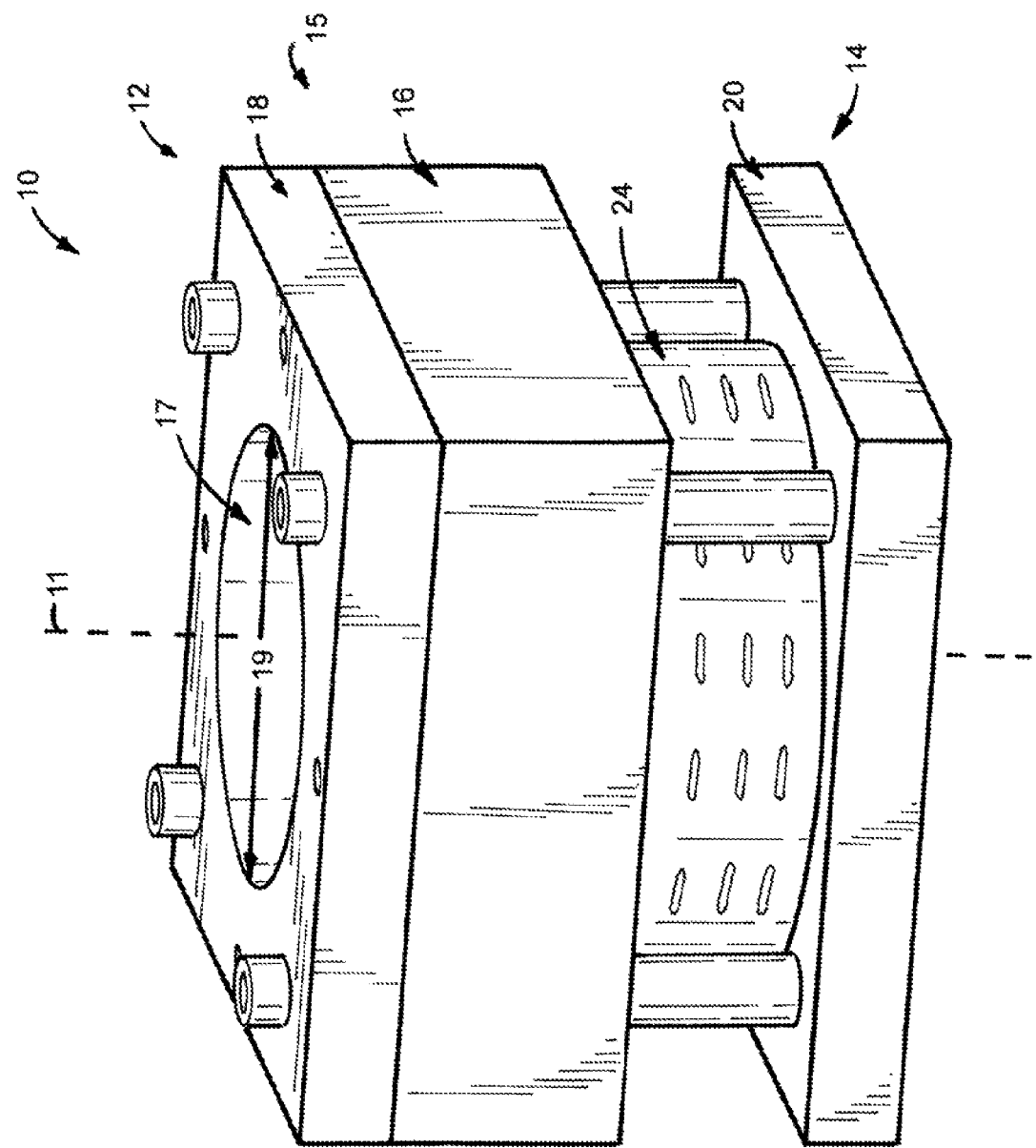
FIG. 1 is a perspective view of an example material processing apparatus. The material processing apparatus includes a first inner member.
Figure 2:
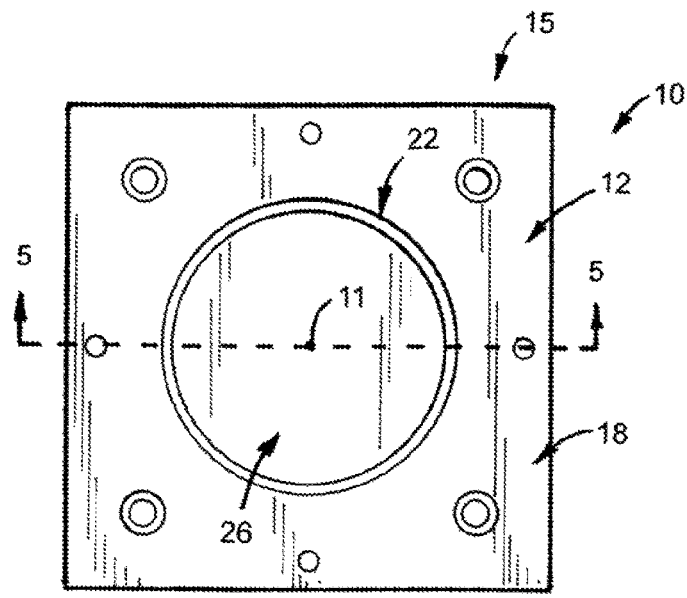
FIG. 2 is a top view of the material processing apparatus illustrated in FIG. 1.
Figure 3:
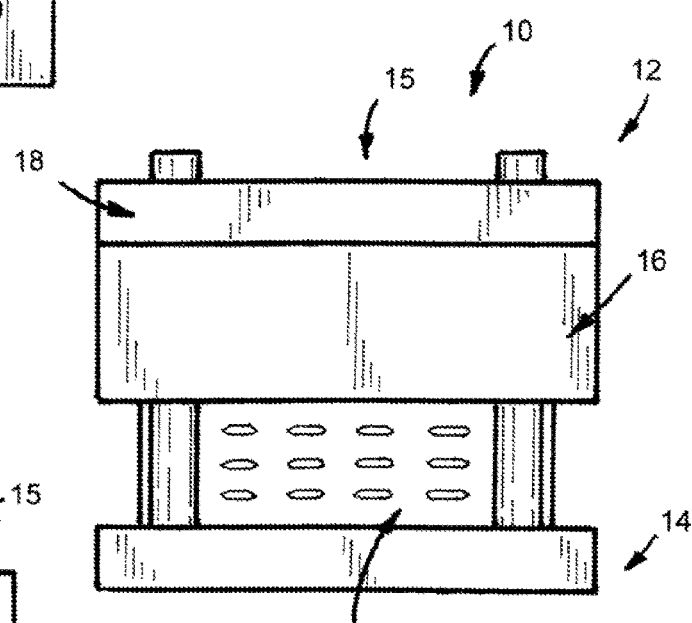
FIG. 3 is an elevation view of the material processing apparatus illustrated in FIG. 1.
Figure 4:
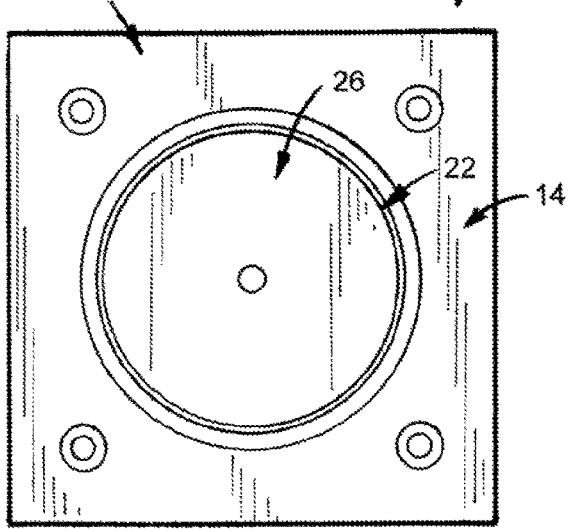
FIG. 4 is a bottom view of the material processing apparatus illustrated in FIG. 1.
Figure 5:
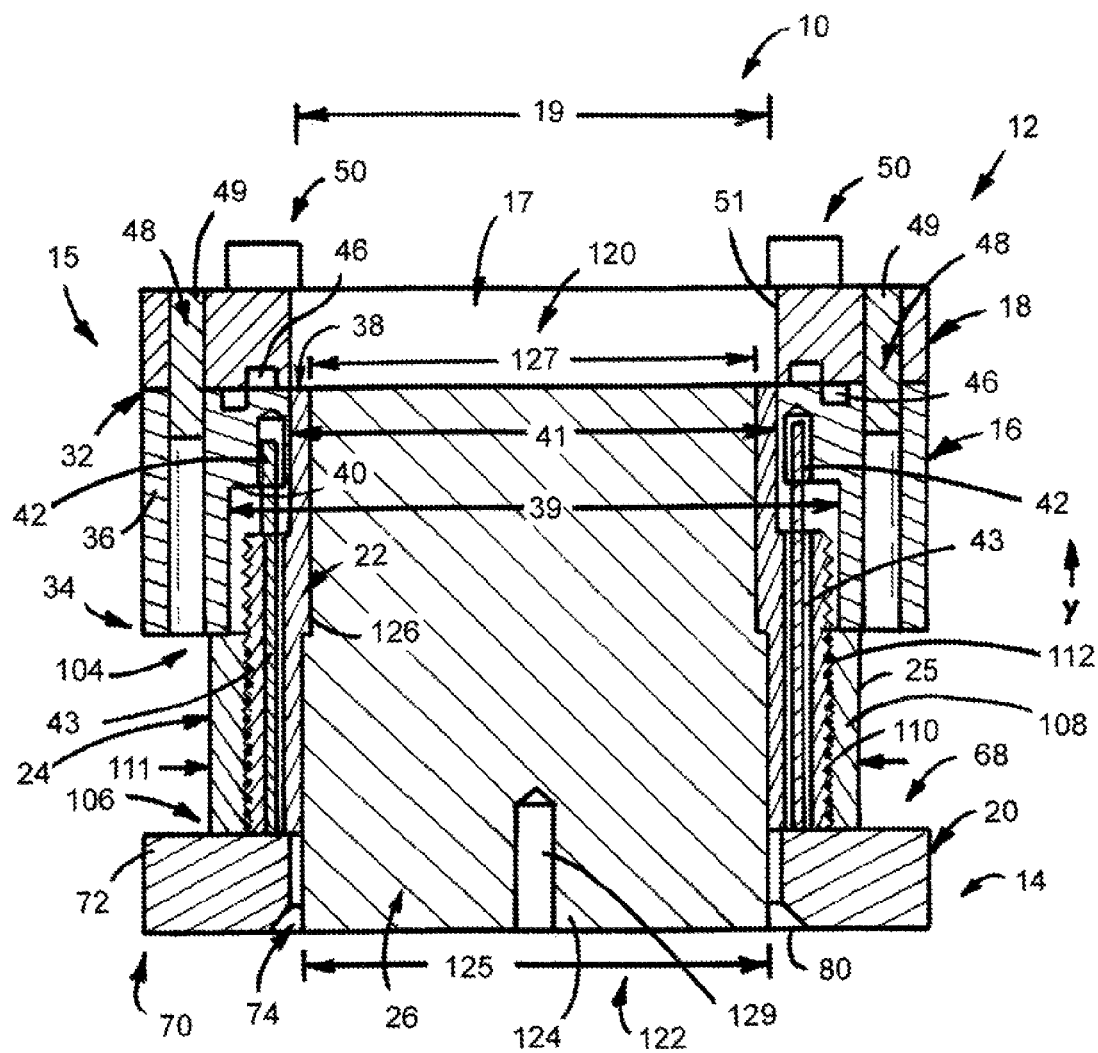
FIG. 5 is a cross-sectional view of the material processing apparatus illustrated in FIG. 2 taken along line 5-5.
Figure 11:
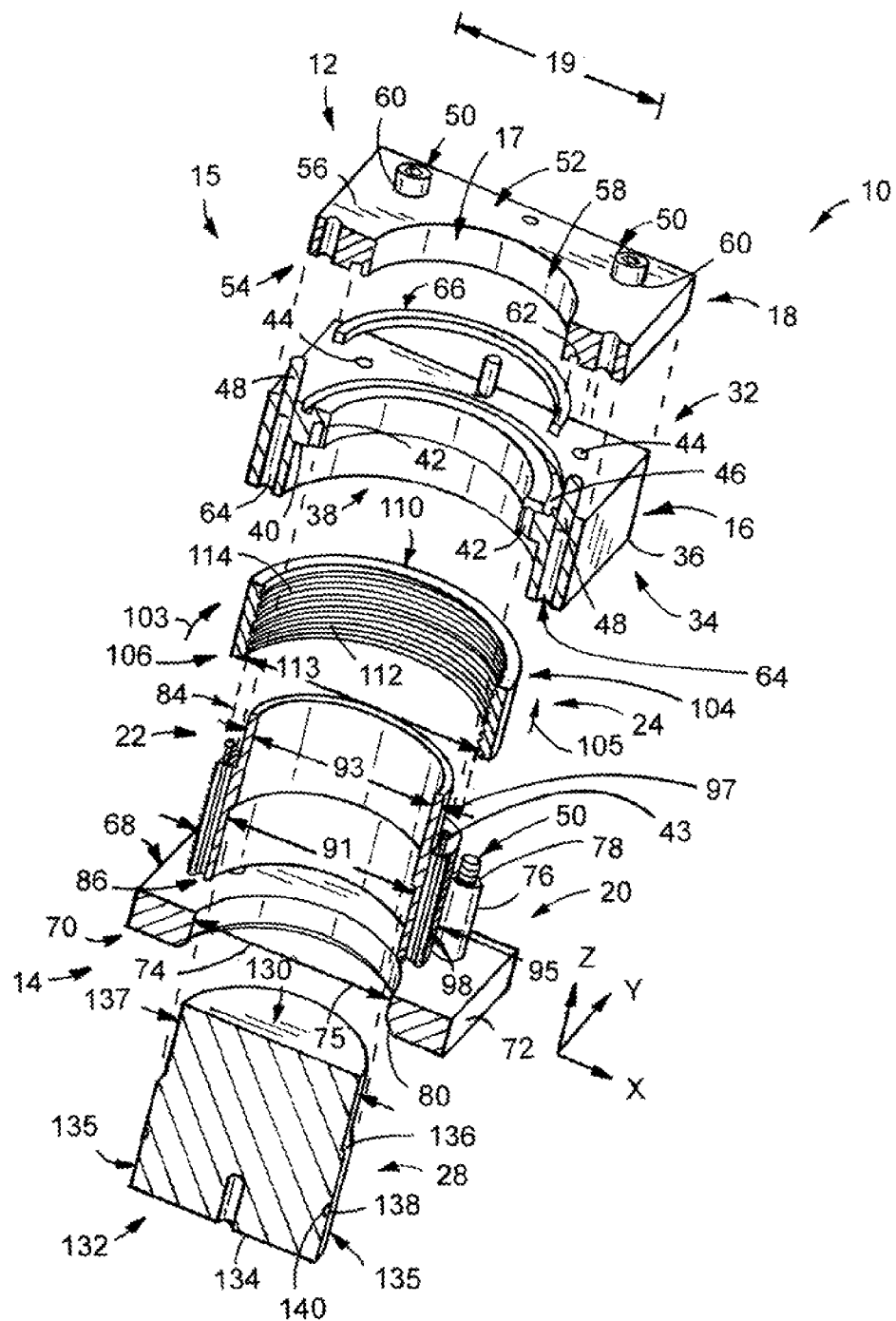
FIG. 11 is an exploded perspective view of the material processing apparatus illustrated in FIG. 8.
Figure 12:
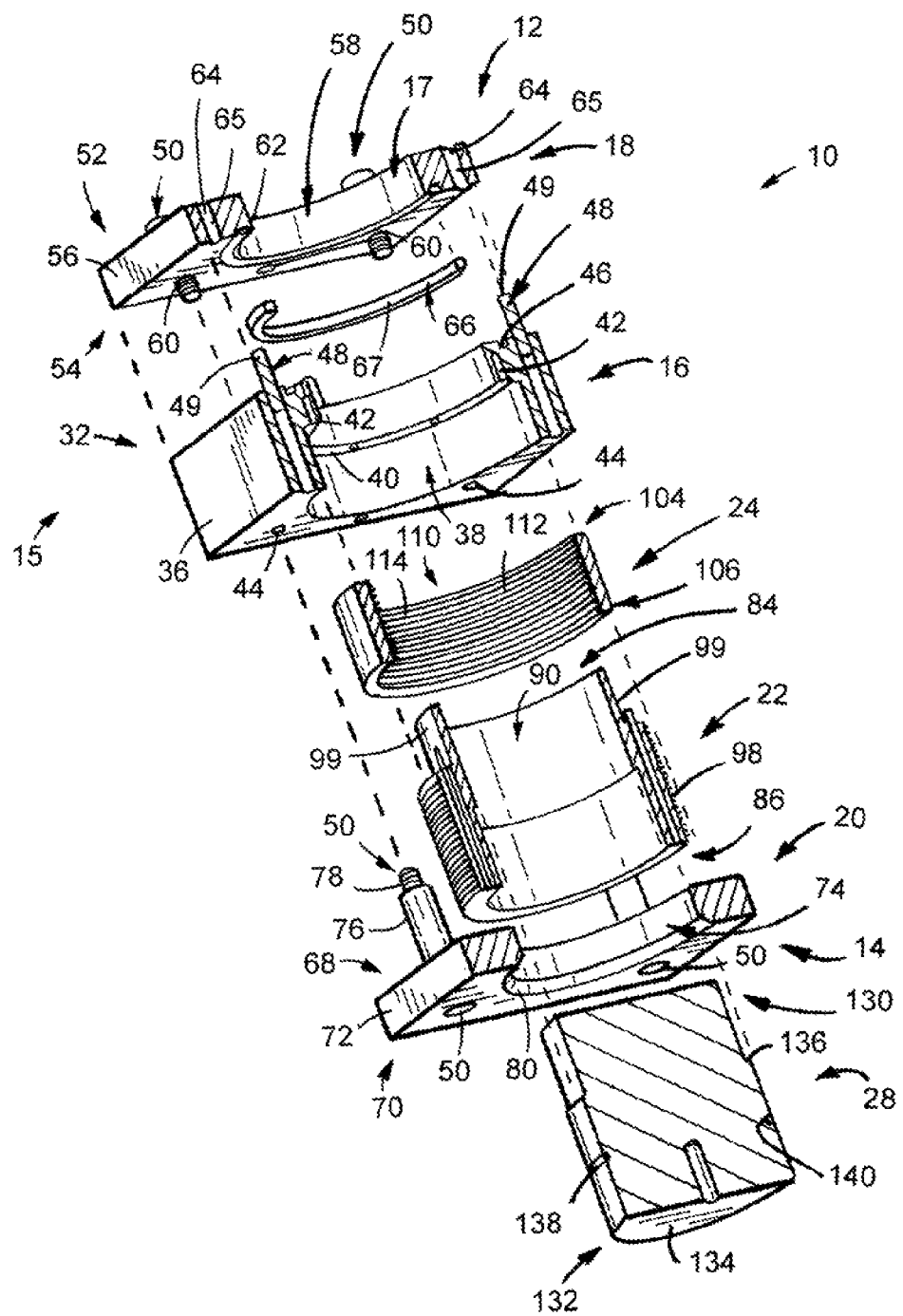
FIG. 12 is another exploded perspective view of the material processing apparatus illustrated in FIG. 8.
Figure 13:
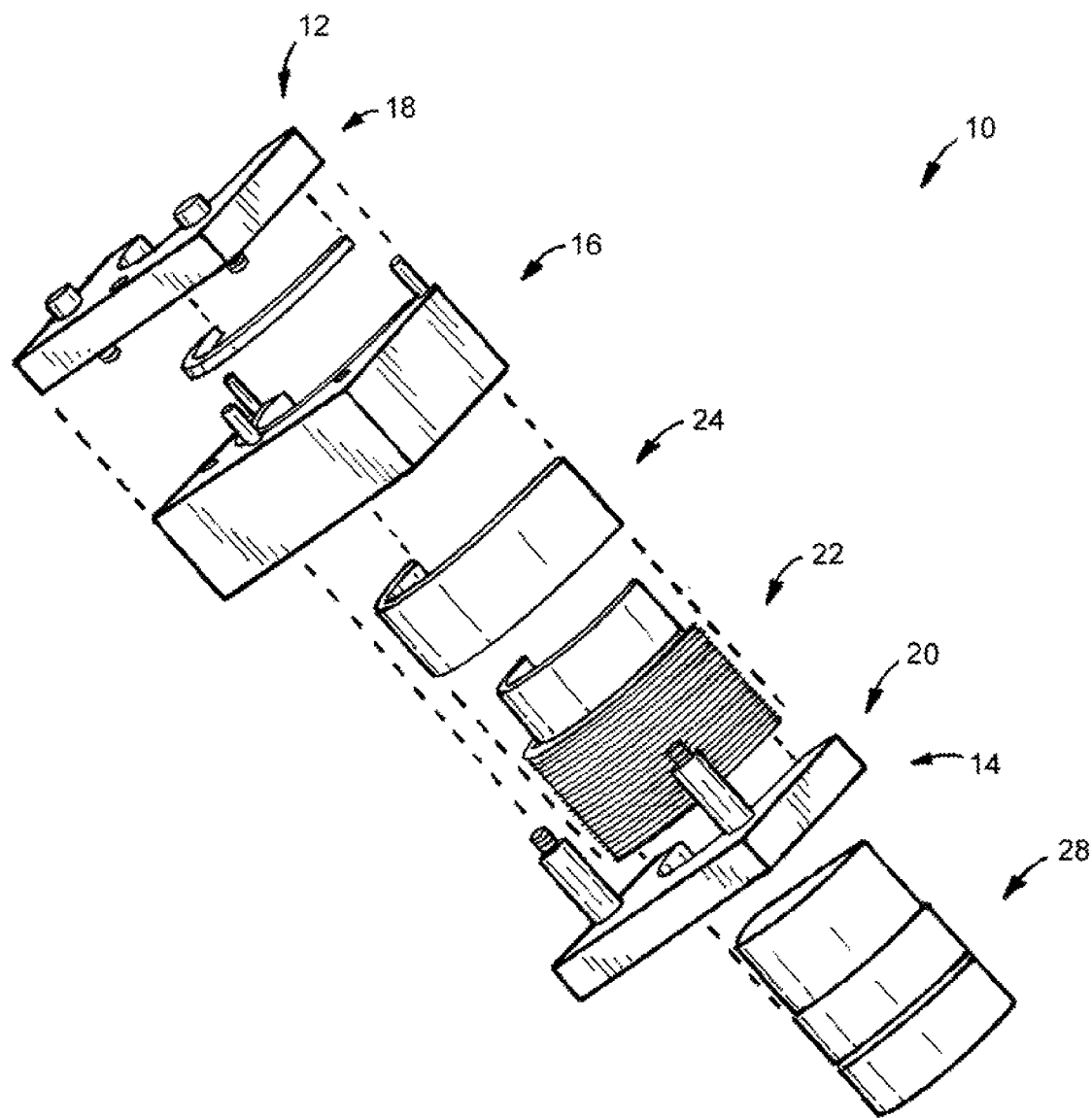
FIG. 13 is another exploded perspective view of the material processing apparatus illustrated in FIG. 8.

In the illustrated embodiment, and as shown in FIGS. 5, 11, and 12, the holding member 15 includes a loading member 16 and a clamping member 18 releasably attached to the loading member 16 and defines a holding member passageway 17 that has an inside diameter 19.

The loading member 16 is disposed on, and contacts, the actuator 24 and has a first end 32, a second end 34, and a main body 36 that defines a loading member passageway 38, a shoulder 40, a plurality of guide recesses 42, a plurality of attachment passageways 44, a recess 46, and a first guide member 48. The loading member passageway 38 extends from the first end 32 to the second end 34 and has a first inside diameter 39 and a second inside diameter 41. The first inside diameter 39 extends from the second end 34 to the shoulder 40. The second inside diameter 41 extends from the shoulder 40 to the first end 32 and is less than the first inside diameter 39. The shoulder 40 is disposed within the loading member passageway 40 and provides a mechanical stop to advancement of the tensioning member 22 through the loading member passageway 38. Each recess of the plurality of guide recesses 42 extends into the main body 36 from the shoulder 40 toward the first end 32 and is sized and configured to receive a portion of a pin 43 to maintain the position (e.g., rotational position) of the loading member 16 relative to the tensioning member 22 about the z-axis during use, as shown in FIG. 11. Alternative embodiments, however, can omit the inclusion of a plurality of guide recesses 42 and pins 43. Each passageway of the plurality of attachment passageways 44 extends through the main body 36 from the first end 32 to the second end 34 and is sized and configured to receive one or more attachment members 50 to accomplish releasable attachment between the loading member 16 and the clamping member 18 and between the loading member 16 and the base 20. The recess 46 surrounds (e.g., circumferentially) the opening of the loading member passageway 38 defined on the first end 32 and is sized and configured to receive a portion of tissue when the tissue is disposed between the loading member 16 and the clamping member 18.

Figure 8:
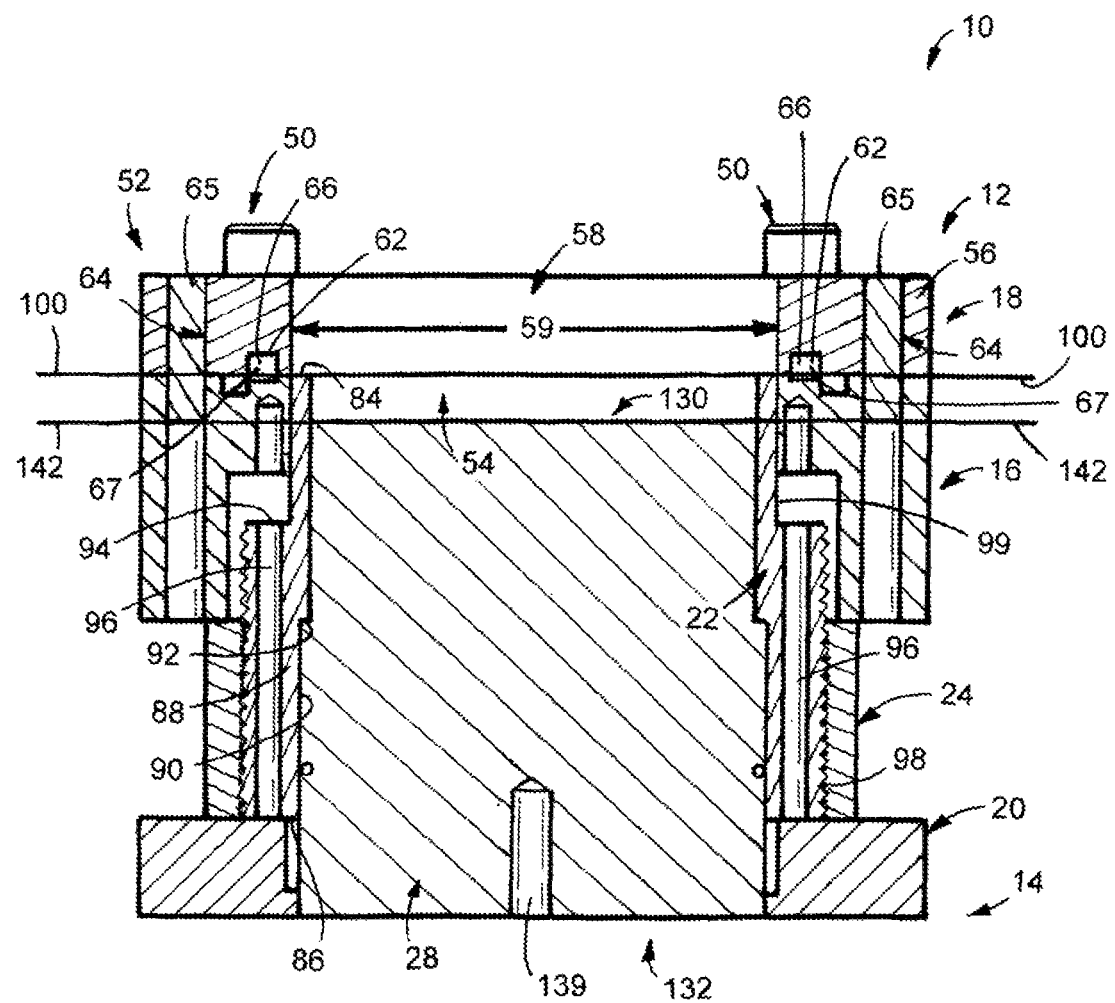
FIG. 8 is a cross-sectional view of the material processing apparatus illustrated in FIG. 2 taken along line 5-5. The material processing apparatus includes a second inner member.
Figure 9:
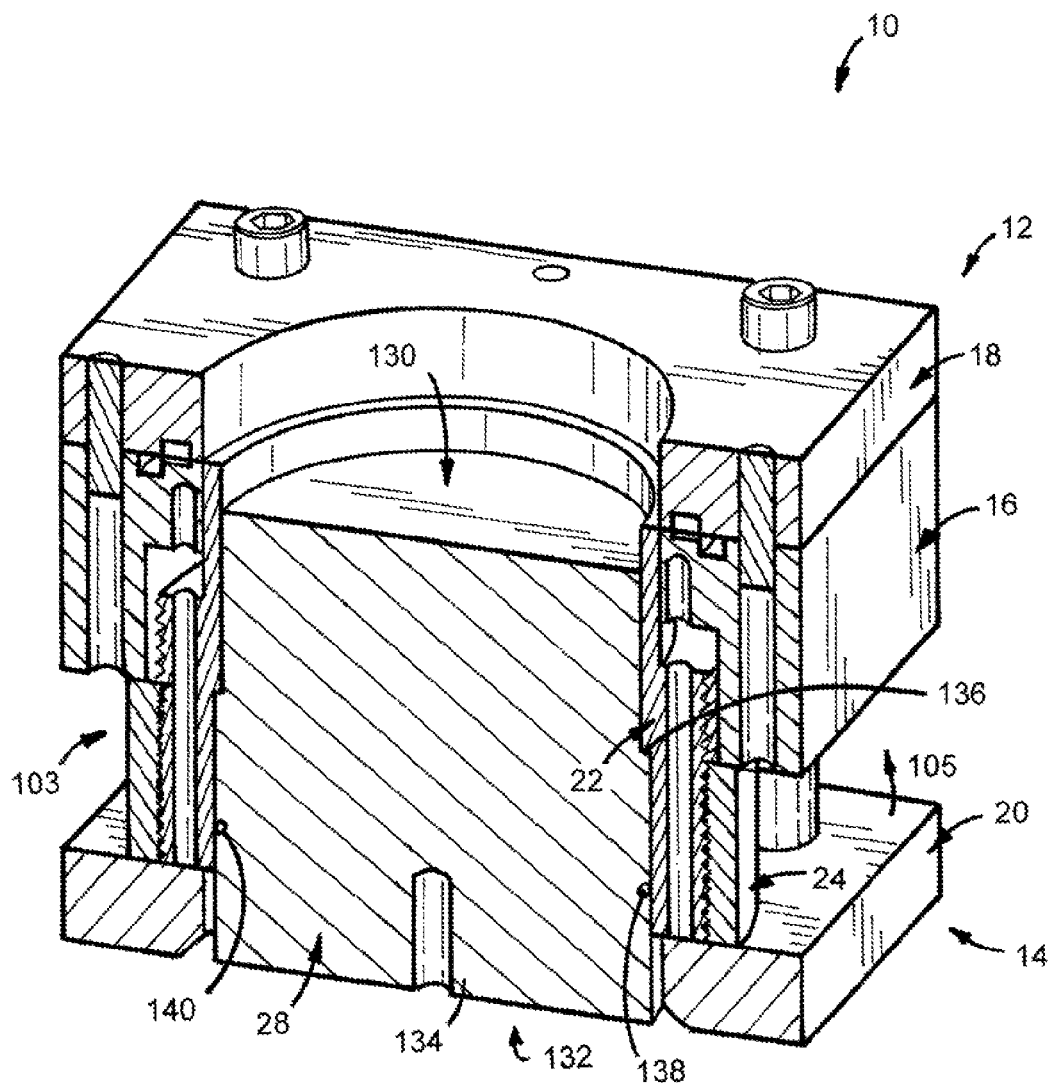
FIG. 9 is a perspective view of the material processing apparatus illustrated in FIG. 8.
Figure 10:
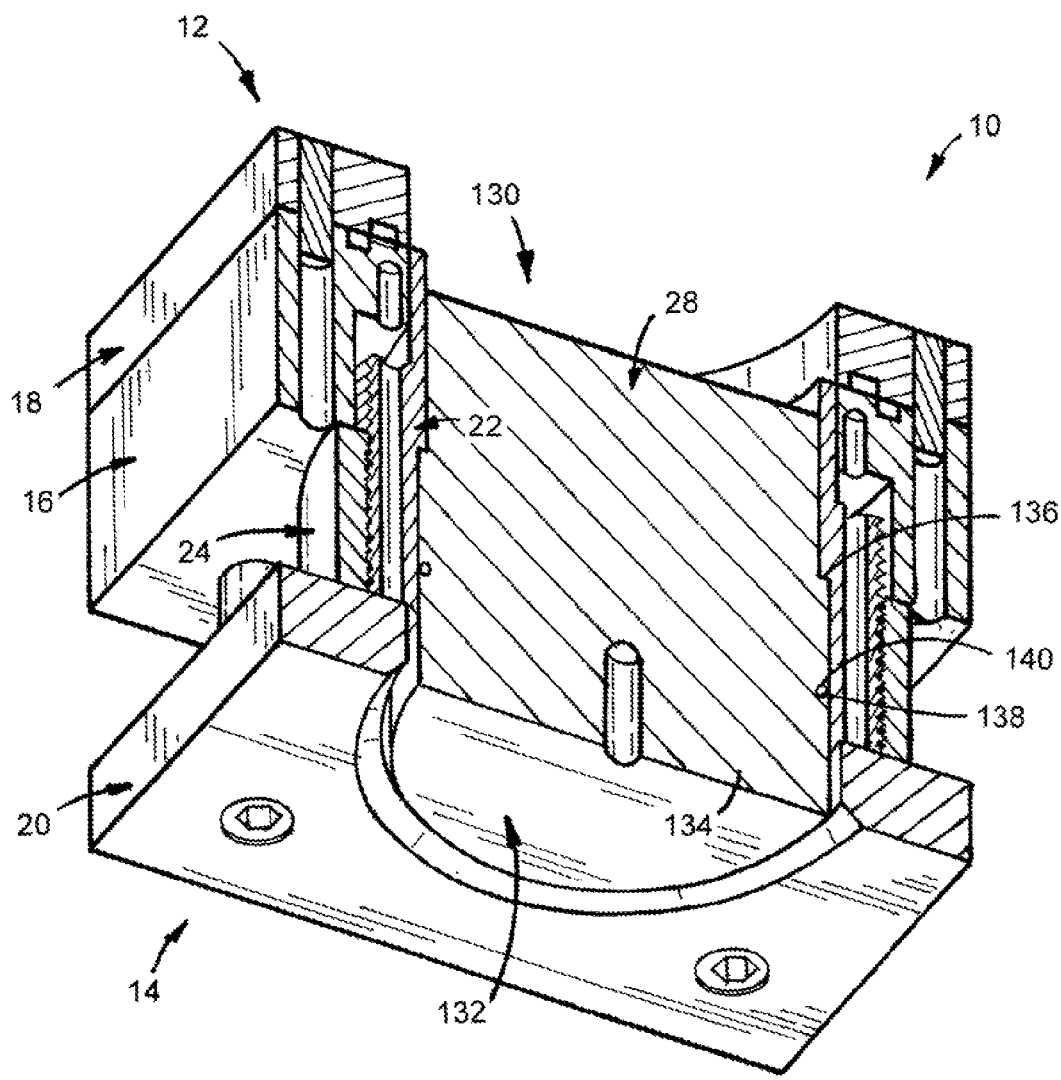
FIG. 10 is another perspective view of the material processing apparatus illustrated in FIG. 8.

In the illustrated embodiment, and as shown in FIGS. 8, 11, and 12, the clamping member 18 is releasably attached to the loading member 16 and has a first end 52, a second end 54, a main body 56, and a gripping member 66. The main body 56 defines a clamping member passageway 58, a plurality of attachment passageways 60, a recess 62, and a second guide member 64. The clamping member passageway 58 extends from the first end 52 to the second end 54 and has an inside diameter 59. The clamping member passageway 58 and the loading member passageway 38 cooperatively define the holding member passageway 17. The inside diameter 59 is greater than the second inside diameter 41 of the loading member 16. Each passageway of the plurality of attachment passageways 60 extends through the main body 56 from the first end 52 to the second end 54 and is sized and configured to receive one or more attachment members 50 to accomplish releasable attachment between the loading member 16 and the clamping member 18. The recess 62 surrounds (e.g., circumferentially) the opening of the clamping member passageway 58 defined on the second end 54 and is sized and configured to receive a portion of the gripping member 66. The gripping member 66 is partially disposed within the recess 62, surrounds the clamping member passageway 58, and provides a mechanism to maintain the position of tissue between the loading member 16 and the clamping member 18 during use. The gripping member 66 is disposed between the loading member 16 and the clamping member 18 when the loading member 16 is releasably attached to the clamping member 18.

A first guide member included on a loading member and a second guide member included on clamping member can include any suitable feature, device, or component capable of maintaining the position of a loading member relative to a clamping member along an x-axis and a y-axis, as shown in FIG. 11, while the clamping member is being attached to the loading member. For example, a loading member can include a first guide member and the clamping member can include a second guide member that mates with the first guide member to prevent movement of the loading member relative to the clamping member along two axes (e.g., the x-axis and the y-axis) during releasable attachment of the clamping member to the loading member. It is considered advantageous to include a first guide member and a second guide member to reduce, or eliminate, any unintentional deformation and/or stress imparted on tissue positioned between a loading member and a clamping member. Selection of suitable first and second guide members to include in a material processing apparatus can be based on various considerations including the intended use of the apparatus. Examples of suitable guide members include a plurality of guide pins and a plurality of guide holes, a first track that is received by a second track, use of one or more magnets, combinations of the guide members described herein, and any other guide member considered suitable for a particular embodiment. In the illustrated embodiment, the first guide member 48 comprises a plurality of guide pins 49 and the second guide member 64 comprises a plurality of guide holes 65. A guide pin of the plurality of guide pins 49 is disposed within a guide hole of the plurality of guide holes 65 when the clamping member 18 is releasably attached to the loading member 16. Each guide hole of the plurality of guide holes 65 is sized and configured to receive a guide pin of the plurality of guide pins 49.

A gripping member included in a material processing apparatus can comprise any suitable feature, device, or component capable of maintaining the position tissue disposed between a loading member and a clamping member when the loading member is releasably attached to the clamping member. Selection of a suitable gripping member to include in a material processing apparatus can be based on various considerations, including the tissue intended on being processed using the material processing apparatus. Examples of suitable gripping members include forming a portion of a loading member or clamping member as a raised projection, forming a recess in a loading member and/or a clamping member and positioning a gasket (e.g., O-ring) or portion of the loading member and/or clamping member within the recess, using a series of pins that maintain the position of tissue during use, and any other gripping member considered suitable for a particular embodiment. In the illustrated embodiment, the gripping member 66 is an O-ring. While a gripping member has been illustrated as surrounding the passageway defined by the clamping member 18, alternative embodiments can include a gripping member that surrounds a passageway defined by a loading member. Alternatively, a material processing apparatus can include a first gripping member on a clamping member, as described herein, and a second gripping member on a loading member, as described herein, that are positioned such that the gripping member of the clamping member mates with the gripping member of the loading member, or such that a gripping member of the clamping member does not contact a gripping member of the loading member, when the clamping member is releasably attached to the loading member.

In the illustrated embodiment, and as shown in FIGS. 5, 11, and 12, the base 20 is releasably attached to the holding member 15 (e.g., loading member 16) and has a first end 68, a second end 70, and a main body 72 that defines a base passageway 74, a plurality of projections 76, and a plurality of attachment passageways 78. The base passageway 74 extends from the first end 68 to the second end 70 and has an inside diameter 75. The base passageway 74 has a tapered opening 80 on the second end 70 of the base 20 that assists with the introduction of an inner member 26, 28, as described in more detail herein. Each projection of the plurality of projections 76 extends from the first end 68 and away from the second end 70. Each passageway of the plurality of attachment passageways 78 extends through the main body 72 from the second end 70 to the first end 68, through a projection of the plurality of projections 76, and is sized and configured to receive one or more attachment members 50 to accomplish releasable attachment between the loading member 16 and the base 20. While the base 20 has been illustrated as releasably attached to the loading member 16, alternative embodiments can include a base that is permanently attached to a loading member (e.g., such that the loading member and base are formed as an integrated component or fixed to one another in a permanent fashion (e.g., fusing)).

An attachment member included in a material processing apparatus can comprise any suitable feature, device, or component capable of providing attachment (e.g., releasable attachment) between two components and selection of a suitable attachment member can be based on various considerations, including the type of attachment desired between two components. Examples of suitable attachment members include any suitable connector and/or adapter, threaded connectors, conical connectors (e.g., cones, sockets), combinations of the attachment members described herein, adhesives, and any other connector and/or adapter considered suitable for a particular embodiment. In the illustrated embodiment, each of the attachment members 50 comprises a threaded connector.

While the loading member 16 has been illustrated as being releasably attached to the clamping member 18 using a plurality of attachment members 50 and the loading member 16 has been illustrated as being releasably attached to the base 20 using a plurality of attachment members 50, a loading member and a clamping member can be releasably attached to one another using any suitable technique or method of attachment and a loading member and a base can be releasably attached to one another using any suitable technique or method of attachment. Selection of a suitable technique or method of attachment between a loading member and a clamping member and/or between a loading member and a base can be based on various considerations, including the material that forms the loading member, the clamping member, and/or the base. Examples of techniques and methods of attachment considered suitable between a loading member and a clamping member and/or between a loading member and a base include using threaded connections, snap fit attachments, using one or more connectors, one or more mating slots and projections, one or more sealed unions, tapered attachments, external clamps, pneumatic clamping mechanisms, adhesives, and any other technique or method of attachment considered suitable for a particular embodiment.

In the illustrated embodiment, and as shown in FIGS. 6, 8, 11, 12, and 14, the tensioning member 22 is moveable between a first position, as shown in FIGS. 5, 6, 7, 8, 9, and 10, and a second position, as shown in FIG. 14, and is partially disposed within the loading member passageway 38. The tensioning member 22 has a first end 84, a second end 86, and a main body 88 that defines a tensioning member passageway 90, a first shoulder 92, a second shoulder 94, a first outside diameter 95, a plurality of guide passageways 96, a second outside diameter 97, a thread 98, and an outer surface 99. The tensioning member passageway 90 extends from the first end 84 to the second end 86 and has a first inside diameter 91 and a second inside diameter 93. In the illustrated embodiment, the loading member passageway 38, the clamping member passageway 58, the base passageway 74, and the tensioning member passageway 90 are coaxial. The first inside diameter 91 extends from the second end 86 to the first shoulder 92. The second inside diameter 93 extends from the first shoulder 92 to the first end 84 and is less than the first inside diameter 91. The first shoulder 92 is disposed within the tensioning member passageway 90 and provides a mechanical stop to advancement of the first inner member 26 and the second inner member 28, as described in more detail herein. The first outside diameter 95 extends from the second end 86 to the second shoulder 94. The second outside diameter 97 extends from the second shoulder 94 to the first end 84, is less than the first outside diameter 95, and is less than the inside diameter 59 of the clamping member passageway 58. This structural arrangement forms a gap 101 between the tensioning member 22 and the clamping member 18 when the tensioning member 22 is in the second position and allows tissue to be disposed between the tensioning member 22 (e.g., outer surface 99 of the tensioning member 22) and the clamping member 18 (e.g., inner surface 51 of the clamping member 18) during use. The second shoulder 94 is disposed between the first end 84 and the second end 86 and provides a mechanical stop to advancement of the tensioning member 22 within the loading member passageway 38, as described in more detail herein. Each passageway of the plurality of guide passageways 96 extends through the main body 88 from the second shoulder 94 to the second end 86 and is sized and configured to receive a portion of a pin 43 to maintain the position (e.g., rotational position) of the tensioning member 22 relative to the loading member 16 about the z-axis, as shown in FIG. 11, during use. Alternative embodiments, however, can omit the inclusion of a plurality of guide passageways 42. The thread 98 is disposed on the outer surface 99 of the tensioning member 22 and is sized and configured to mate with the thread 112 defined by the actuator 24, as described in more detail herein, to move of the tensioning member between the first position and the second position.

The tensioning member 22 is moveable relative to the loading member 16, the clamping member 18, and the base 20. In the first position, the tensioning member 22 is disposed on, and contacts, the base 20 and the first end 84 (e.g., end surface) of the tensioning member 22 is disposed on a first hypothetical plane 100, as shown in FIG. 8, that contains the first end 32 (e.g., end surface) of the loading member 16. However, alternative embodiments can include a tensioning member that in the first position has a first end (e.g., end surface) disposed near a first hypothetical plane (e.g., within about 1 millimeter of the hypothetical plane) that contains a first end (e.g., end surface) of a loading member. When the actuator 24 is moved in the first direction 103, the tensioning member 22 is moved from the first position toward the second position such that the first end 84 of the tensioning member 22 moves away from the base 20 and toward the first end 52 of the clamping member 18. In the second position, the tensioning member 22 is free of contact with the base 20 and the first end 84 (e.g., end surface) of the tensioning member 22 is disposed on a second hypothetical plane 102, as shown in FIG. 14, that is disposed within (e.g., extends through the cross-section of) the clamping member passageway 58. Alternatively, depending on the structural configuration of a clamping member included in a material processing apparatus, in the second position, a tensioning member can be free of contact with a base and the first end of the tensioning member can be disposed on a second hypothetical plane that is disposed outside of a clamping member passageway such that the tensioning member is disposed outside of the clamping member passageway. The position of the first end 84 of the tensioning member 22 when the tensioning member 22 is in the second position can be based on a desired amount of stretch intended to be imparted on the tissue being processed. When the actuator 24 is moved in the second direction 105, the tensioning member 22 is moved from the second position toward the first position such that the first end 84 of the tensioning member 22 moves toward the base 20. While the first end 84 of the tensioning member 22 has been illustrated as being disposed on a plane, alternative embodiments can include a tensioning member that includes a rounded first end, a first end that defines a recess, or any other suitable tensioning member.

In the illustrated embodiment, and as shown in FIGS. 5, 9, 11, and 12, the actuator 24 is disposed on, and contacts, the base 20 between the loading member 16 and the base 20, contacts the loading member 16 and the base 20, is moveably attached to the tensioning member 22, and is movable in a first direction 103 and a second direction 105. Movement of the actuator 24 results in movement of the tensioning member 22 between its first position and second position. The actuator 24 has a first end 104, a second end 106, and a main body 108 that defines an actuator passageway 110, an outside diameter 111, and a thread 112. The actuator passageway 110 extends from the first end 104 to the second end 106 and has an inside diameter 113. The outside diameter 111 is greater than the first inside diameter 39 of the loading member 16. The inside diameter 113 is equal to about the first outside diameter 95 of the tensioning member 22. The thread 112 is disposed on an inner surface 114 of the actuator 24 and is sized and configured to mate with the thread 98 of the tensioning member 22 to move the tensioning member 22 between the first position and the second position. Optionally, a material processing apparatus can include a locking mechanism that interacts with the tensioning member and the actuator such that they can be releasably fixed to one another and accomplish constant tensioning throughout processing. For example, a set screw that passes through passageway defined by an actuator can contact the tensioning member such that they are releasably fixed to one another.

Any suitable actuator can be included in a material processing apparatus and selection of a suitable actuator can be based on various considerations, including the structural arrangement of a tensioning member included in the material processing apparatus. Examples of actuators considered suitable for inclusion in a material processing apparatus include linear actuators, rotatable actuators, manually operated actuators, automated actuators, worm drives, combinations of the actuators described herein, and any other actuator considered suitable for a particular embodiment. In the illustrated embodiment, the actuator 24 comprises a rotatable actuator 25 that is manually operated and rotatably attached to the tensioning member 22. The interaction between thread 98 and thread 112 provides a mechanism for achieving a high level of precision when regulating the amount of tension being applied to tissue during processing.

Figure 6:
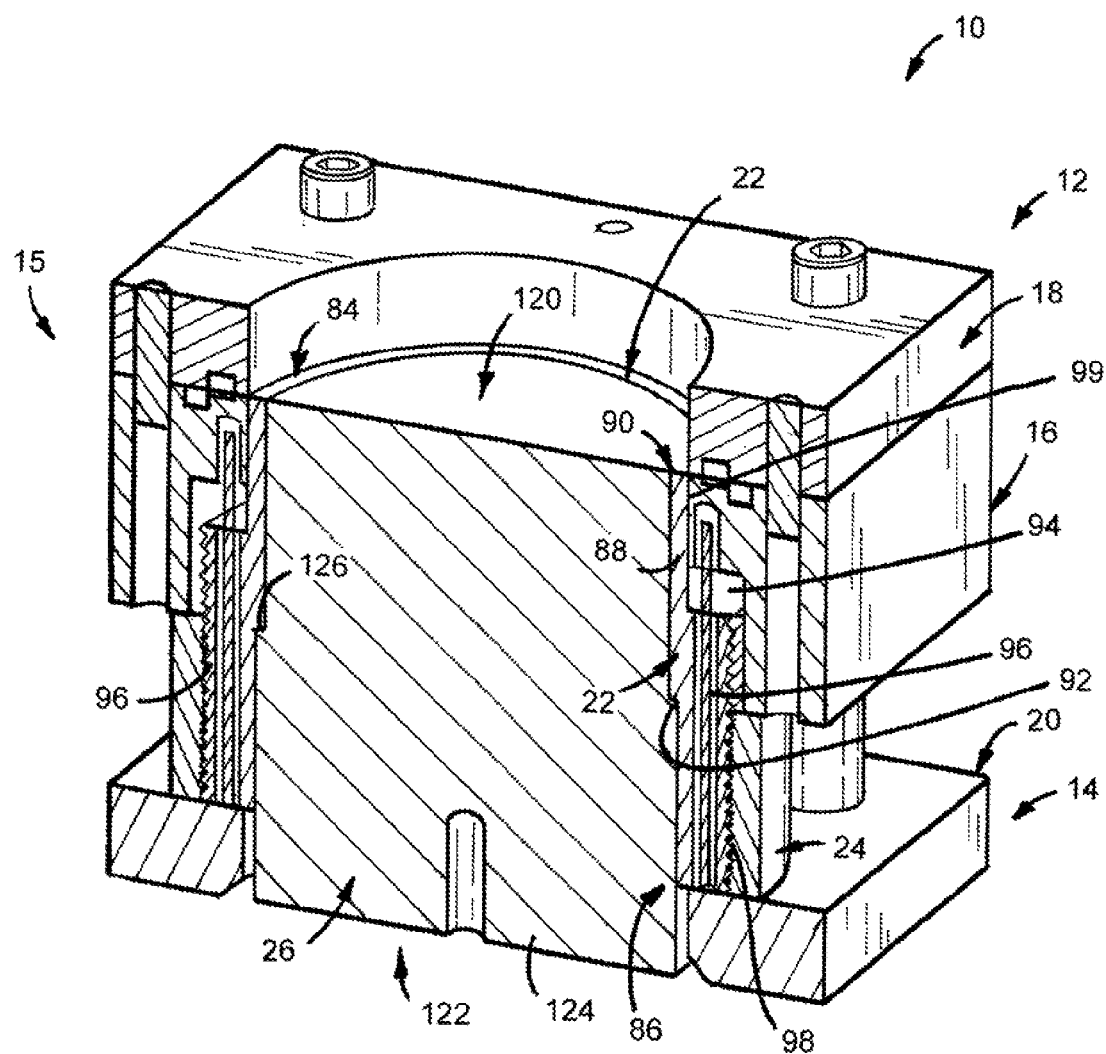
FIG. 6 is a perspective view of the material processing apparatus illustrated in FIG. 5.
Figure 7:
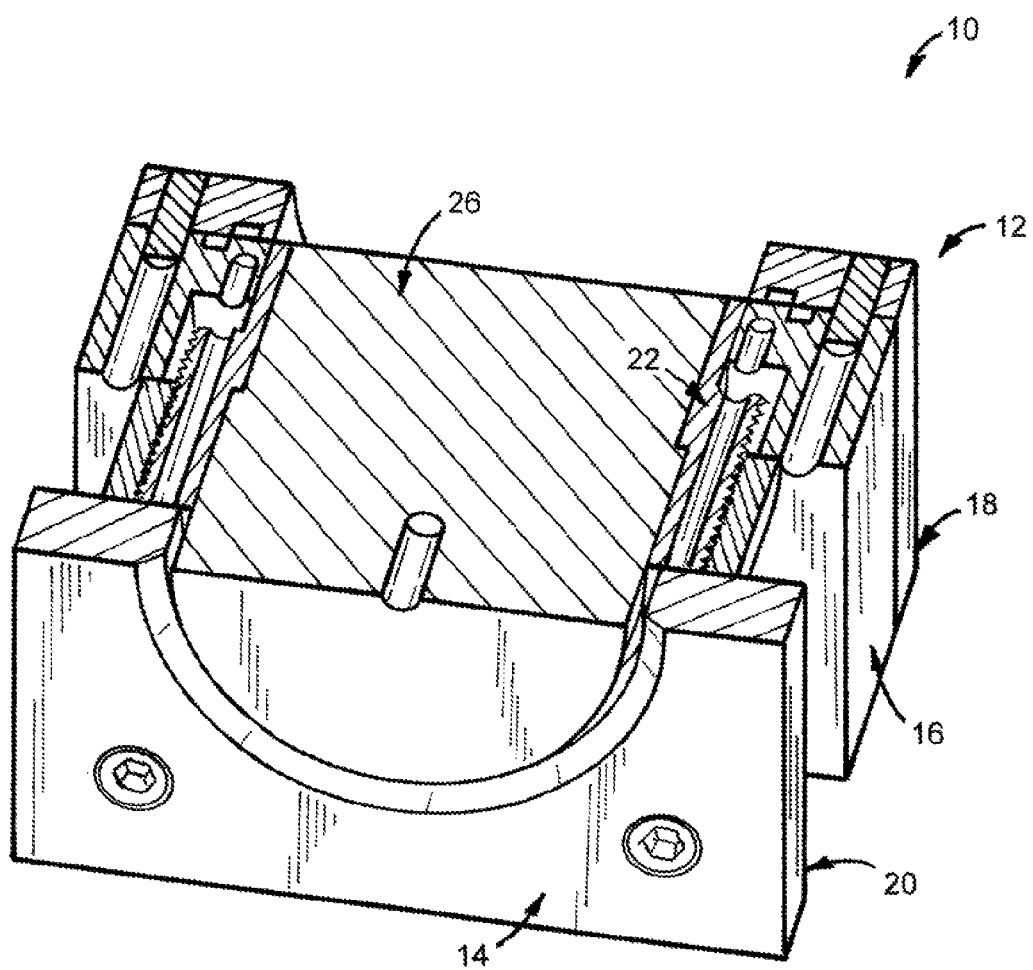
FIG. 7 is another perspective view of the material processing apparatus illustrated in FIG. 5.

In the illustrated embodiment, and as shown in FIGS. 5 and 6, the first inner member 26 is adapted to be disposed within the base passageway 74 and the tensioning member passageway 90. The first inner member 26 has a first end 120, a second end 122, and a main body 124 that defines a shoulder 126, a first outside diameter 125, a second outside diameter 127, and a threaded recess 129. The shoulder 126 is disposed between the first end 120 and the second end 122 and interacts with the first shoulder 92 defined by the tensioning member 22 such that a mechanical stop to advancement of the first inner member 26 beyond the first shoulder 92 defined by the tensioning member 22 can be achieved. The first outside diameter 125 extends from the second end 122 to the shoulder 126 and is equal to about the first inside diameter 91 of the tensioning member 22. The second outside diameter 127 extends from the shoulder 126 to the first end 120, is less than the first outside diameter 125, and is equal to about the second inside diameter 93 of the tensioning member 22. The threaded recess 129 extends from the second end 122 toward the first end 120 and is sized and configured to receive a threaded member (e.g., set screw) such that the first inner member 26 can be positioned within the base passageway 74 and the tensioning member passageway 90 and withdrawn from the base passageway 74 and the tensioning member passageway 90 when desired. Alternative embodiments, however, can include any suitable structure capable of providing a mechanism for positioning an inner member within a base passageway and a tensioning member passageway and withdrawing the inner member when desired. When disposed within the base passageway 74 and the tensioning member passageway 90, the material processing apparatus 10 is disposed on a flat surface, and the tensioning member 22 is in the first position, the first end 120 (e.g., end surface) of the first inner member 26 is disposed on the first hypothetical plane 100 that contains the first end 32 (e.g., end surface) of the loading member 16 and the first end 84 (e.g., end surface) of the tensioning member 22. This structural arrangement allows for placement of tissue on the loading member 16, tensioning member 22, and the first inner member 26, as described in more detail herein. However, alternative embodiments can include an inner member that when disposed within a base passageway and a tensioning member passageway, the material processing apparatus is disposed on a flat surface, a first end (e.g., end surface) of the first inner member is disposed near a first hypothetical plane (e.g., within about 1 millimeter of the hypothetical plane) that contains a first end (e.g., end surface) that contains a first end (e.g., end surface) of a loading member.

In the illustrated embodiment, and as shown in FIGS. 8, 9, 11, 12, and 14, the second inner member 28 is adapted to be disposed within the base passageway 74 and the tensioning member passageway 90. The second inner member 28 has a first end 130, a second end 132, a main body 134, and a gripping member 138. The main body 134 defines a shoulder 136, a recess 140, a first outside diameter 135, a second outside diameter 137, and a threaded recess 139. The shoulder 136 is disposed between the first end 130 and the second end 132 and interacts with the first shoulder 92 defined by the tensioning member 22 such that a mechanical stop to advancement of the second inner member 28 beyond the first shoulder 92 defined by the tensioning member 22 can be achieved. The first outside diameter 135 extends from the second end 132 to the shoulder 136 and is equal to about the first inside diameter 91 of the tensioning member 22. The second outside diameter 137 extends from the shoulder 136 to the first end 130, is less than the first outside diameter 135, and is equal to about the second inside diameter 93 of the tensioning member 22. The recess 140 extends into the main body 134 between the shoulder 136 and the second end 132 and is sized and configured to receive a portion of the gripping member 138. The threaded recess 139 extends from the second end 132 toward the first end 130 and is sized and configured to receive a threaded member (e.g., set screw) such that the second inner member 28 can be positioned within the base passageway 74 and the tensioning member passageway 90 and withdrawn from the base passageway 74 and the tensioning member passageway 90 when desired. Alternative embodiments, however, can include any suitable structure capable of providing a mechanism for positioning an inner member within a base passageway and a tensioning member passageway and withdrawing the inner member when desired. The gripping member 138 is disposed within the recess 140 and between the second inner member 28 and the tensioning member 22 when the second inner member 28 is disposed within the base passageway 74 and the tensioning member passageway 90. In the illustrated embodiment, the gripping member 138 surrounds the second inner member 28 and provides a mechanism to maintain the position of the second inner member 28 relative to the tensioning member 22 during use, as described in more detail herein. For example, during movement of the tensioning member 22 from its first position to its second position, and vice versa, the gripping member 138 maintains the position of the second inner member 28 relative to the tensioning member 22 such that they translate in unison and the position of the second end 132 (e.g., end surface) of the second inner member 28 is disposed a constant distance from the first end 84 (e.g., end surface) of the tensioning member 22. Optionally, a material processing apparatus can be included in a kit that includes a plurality of second inner members that each have a different height extending from the first end of the second inner member to the second end of the inner member such that a desired amount of stretch can be imparted on a tissue during processing.

Figure 30:
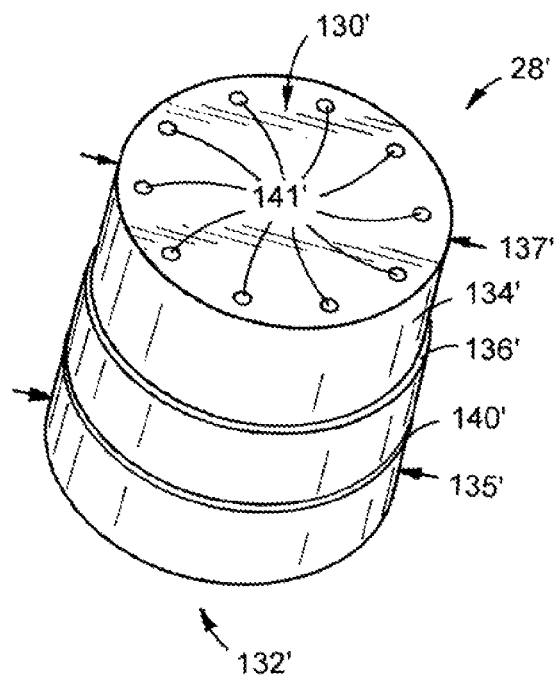
FIG. 30 is a perspective view of an alternative inner member.
Figure 31:
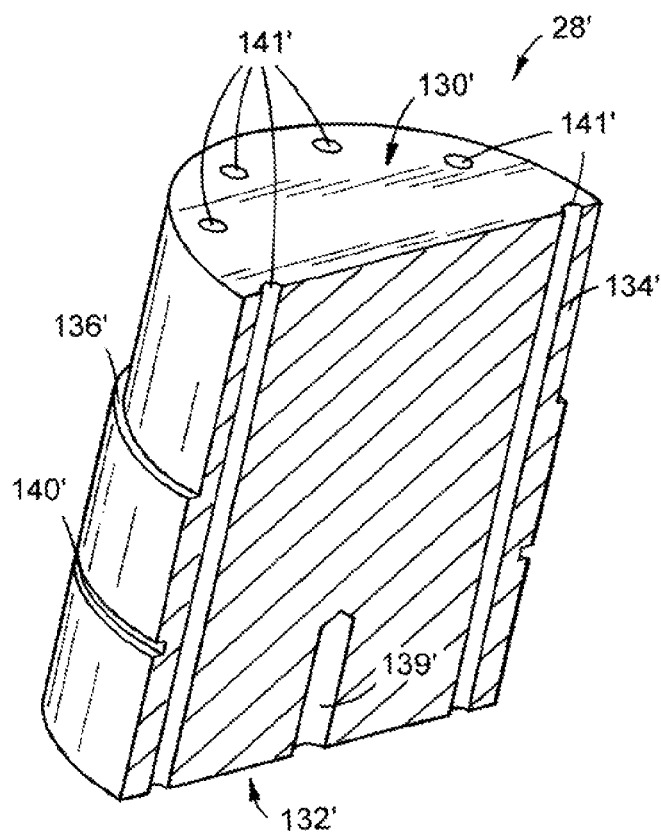
FIG. 31 is a perspective sectional view of the inner member illustrated in FIG. 30 taken along the lengthwise axis of the inner member.

Optionally, an inner member (e.g., first inner member, second inner member) can include one or more through holes that extend from the first end to the second end to prevent suction against any tissue disposed within a material processing apparatus when an inner member is positioned within, withdrawn from, or moved within a base passageway and/or a tensioning member passageway. FIGS. 30 and 31 illustrate an example second inner member 28' that has a first end 130', a second end 132', and a main body 134' that defines a shoulder 136', a recess 140', a first outside diameter 135', a second outside diameter 137', a threaded recess 139', and a plurality of through holes 141'. Each through hole of the plurality of through holes 141' extends from the first end 130' to the second end 132'.

When disposed within the base passageway 74 and the tensioning member passageway 90, and the material processing apparatus 10 is disposed on a flat surface, the first end 130 (e.g., end surface) of the second inner member 28 is disposed on the third hypothetical plane 142, as shown in FIGS. 8 and 14, that is disposed within the tensioning member passageway 90 between the first end 32 of the loading member 16 and the second end 86 of the tensioning member 22. This structural arrangement allows tissue to sag from the first end 84 of the tensioning member 22 toward the second inner member 28, and, depending on the type of tissue and the weight being applied to the tissue, as described in more detail herein, contact the second inner member 28. The first end of a second inner member can be disposed any suitable distance from a tensioning member first end. Examples of suitable distances include 1 millimeter, 2 millimeters, 3 millimeters, 4 millimeters, 5 millimeters, 6 millimeters, 7 millimeters, 8 millimeters, 9 millimeters, 10 millimeters, more than 10 millimeters, and any other distance considered suitable for a particular embodiment.

In an alternative embodiment, a first inner member, or a second inner member that has the same length of a first inner member from the first end to the second end, can include structure that provides a mechanism for the inner member to move relative to a tensioning member between a first position (e.g., the first end of the inner member is disposed on, or near, the hypothetical plane(s) described herein) and a second position (e.g., the first end of the inner member is disposed on a hypothetical plane that is positioned between the first hypothetical plane and the second end of the base). For example, a tensioning member can define a slotted groove that mates with a projection that extends from an outer surface of an inner member to provide a mechanism to move the inner member relative to the tensioning member.

A loading member, a clamping member, a base, a tensioning member, an actuator, a first inner member, and a second inner member, or portions of a loading member, a clamping member, a base, a tensioning member, an actuator, a first inner member, and a second inner member, or any other portion of a material processing apparatus of the embodiments described herein, can be formed of any suitable material and using any suitable technique or method of manufacture. Selection of a suitable material and of a suitable technique or method of manufacture can be based on various considerations, including the intended use of the material processing apparatus. Examples of materials considered suitable to form a loading member, a clamping member, a base, a tensioning member, an actuator, a first inner member, and/or a second inner member of the embodiments described herein include biocompatible materials, materials that can be made biocompatible, metals, such as 316 stainless and 304 stainless, corrosion resistant materials, plastics, polymers, polyethylene, such as high-density polyethylene (HDPE), polypropylene, polycarbonates, silicone, Delrin, transparent materials, opaque materials, combinations of the materials described herein, and any other material considered suitable for a particular embodiment.

The material processing apparatuses, systems, methods, and products described herein, are considered advantageous at least because they provide a mechanism for loading tissue in a resting state, applying a uniform stress on the tissue that can account for the inherent variability in the starting mechanical properties of the tissue that may vary among different sheets of tissue, and for processing of tissue under controlled, uniform tension. In addition, the overall time required to both set up and tear down the apparatuses described herein is reduced relative to differential pressure fixation apparatuses and the processing of tissue results in a tissue product that will be relatively flat subsequent to processing. For example, the material processing apparatus described herein provide several benefits relative to differential pressure processing, such as preventing a domed radius from being formed on the tissue, not requiring active monitoring, and being a passive approach to processing tissue.

Figure 15:
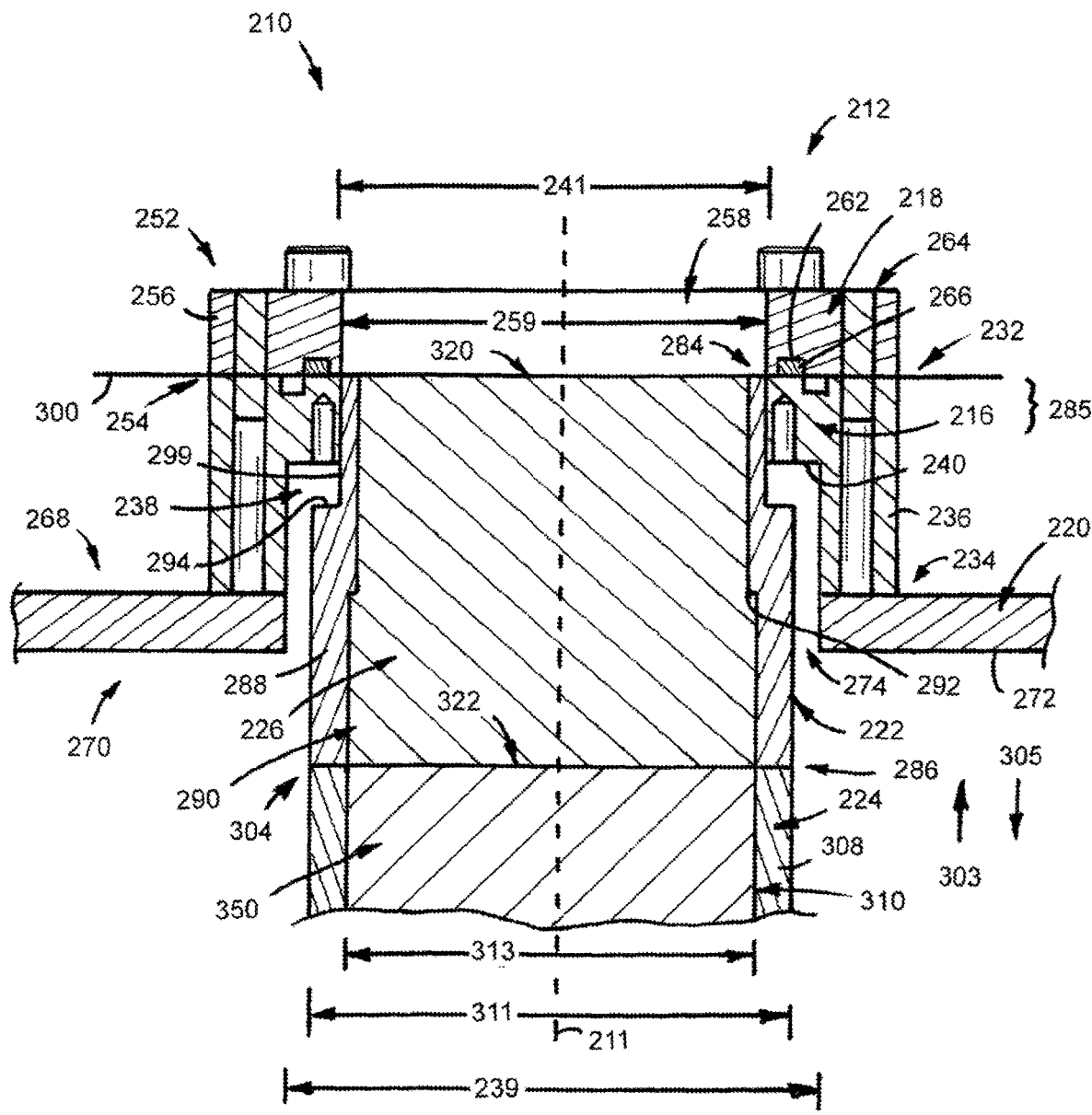
FIG. 15 is a partial sectional view of another example material processing apparatus taken along a plane that contains the lengthwise axis of the material processing apparatus. The material processing apparatus is in the loading configuration.
Figure 16:
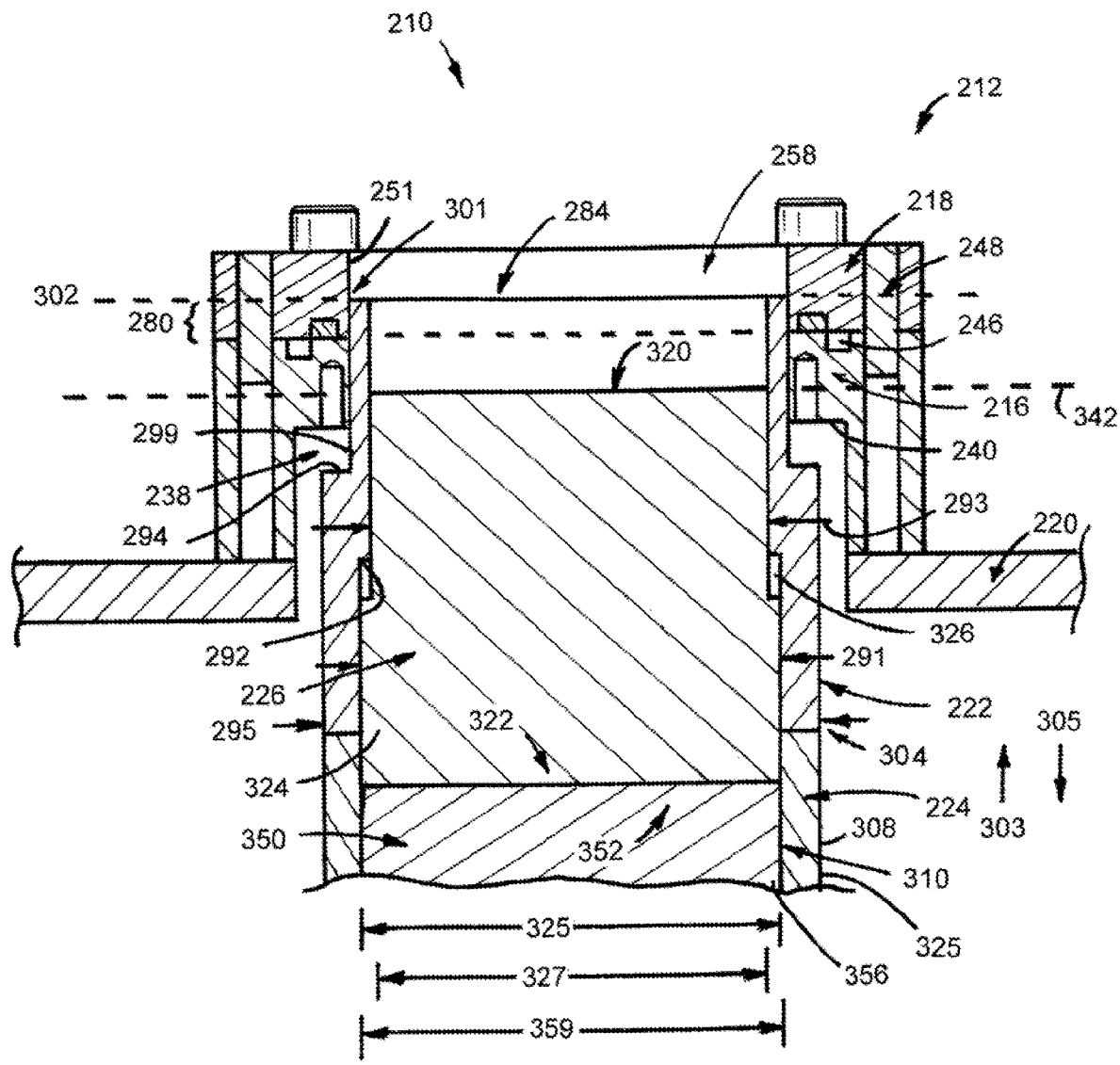
FIG. 16 illustrates the material processing apparatus shown in FIG. 15 in the tensioning configuration.

FIGS. 15 and 16 illustrates another example material processing apparatus 210. The material processing apparatus 210 is similar to the material processing apparatus 10 illustrated in FIGS. 1, 2, 3, 4, 5, 6, 7, 8, 9, 10, 11, 12, 13, and 14 and described above, except as detailed below. The material processing apparatus 210 has a lengthwise axis 211, a first end 212, a second end (not shown), and includes a loading member 216, a clamping member 218, a base 220, a tensioning member 222, a first actuator 224, an inner member 226, and a second actuator 350. The material processing apparatus 210 is moveable between a loading configuration, as shown in FIG. 15, and a tensioning configuration, as shown in FIG. 16.

In the illustrated embodiment, the loading member 216 is attached to the base 220 and has a first end 232, a second end 234, and a main body 236 that defines a loading member passageway 238, a shoulder 240, a recess 246, and a first guide member 248. The clamping member 218 is releasably attached to the loading member 216 and has a first end 252, a second end 254, a main body 256, and a gripping member 266. The main body 256 of the clamping member 218 defines a clamping member passageway 258, a recess 262, and a second guide member 264. The clamping member passageway 258 extends from the first end 252 to the second end 254 and has an inside diameter 259 that is equal to about the second inside diameter 241 of the loading member 216. The base 220 is attached to the loading member 216 (e.g., using adhesive) and has a first end 268, a second end 270, and a main body 272 that defines a base passageway 274.

The tensioning member 222 is moveable between a first position, as shown in FIG. 15, and a second position, as shown in FIG. 16, and is partially disposed within the loading member passageway 238. The tensioning member 222 has a first end 284, a second end 286, and a main body 288 that defines a tensioning member passageway 290, a first shoulder 292, a second shoulder 294, and an outer surface 299. In the illustrated embodiment, the loading member passageway 238, the clamping member passageway 258, the base passageway 274, and the tensioning member passageway 290 are coaxial. The first shoulder 292 is disposed within the tensioning member passageway 290, interacts with the shoulder 326 defined by the inner member 226, and provides a mechanical stop to advancement of the inner member 226 beyond the first shoulder 292. The outside diameter of the tensioning member 222 tapers from a location between the second shoulder 294 and the second end 286 forming a tapered distal portion 285 on the tensioning member 222. This structural arrangement forms a gap 301 between the tensioning member 222 and the clamping member 218 when the tensioning member 222 is in the second position, as shown in FIG. 16, and allows tissue to be disposed between the tensioning member 222 (e.g., outer surface 299 of the tensioning member 222) and the clamping member 218 (e.g., inner surface 251 of the clamping member 218) during use. The second shoulder 294 interacts with the shoulder 240 defined by the loading member 216 and provides a mechanical stop to advancement of the tensioning member 222 within the loading member passageway 238.

While the first shoulder 292 has been illustrated as being disposed within the tensioning member passageway 290 such that it interacts with the shoulder 326 defined by the inner member 226 and provides a mechanical stop to advancement of the inner member 226 beyond the first shoulder 292, a material processing apparatus can omit the inclusion of a shoulder on a tensioning member and/or an inner member. For example, the position of a first end of an inner member relative to the first end of a tension member and/or loading member can be controlled using an actuator, such as those described herein, or any other structure incorporated into a tensioning member and/or inner member (e.g., slot and pins).

The tensioning member 222 is moveable relative to the loading member 216, the clamping member 218, and the base 220. In the first position, the first end 284 (e.g., end surface) of the tensioning member 222 is disposed on a first hypothetical plane 300, as shown in FIG. 15, that contains the first end 232 (e.g., end surface) of the loading member 216. When the actuator 224 is moved in the first direction 303, the tensioning member 222 is moved from the first position toward the second position such that the first end 284 of the tensioning member 222 moves away from the base 220 and toward the first end 252 of the clamping member 218. In the second position, the first end 284 (e.g., end surface) of the tensioning member 222 is disposed on a second hypothetical plane 302, as shown in FIG. 16, that is disposed within (e.g., extends through the cross-section of) the clamping member passageway 258. Alternatively, depending on the structural configuration of a clamping member included in a material processing apparatus, in the second position, the first end of a tensioning member can be disposed on a second hypothetical plane that is disposed outside of a clamping member passageway such that the tensioning member is disposed outside of the clamping member passageway. The position of the first end 284 of the tensioning member 222 when the tensioning member 222 is in the second position can be based on a desired amount of stretch intended to be imparted on the tissue being processed. When the actuator 224 is moved in the second direction 305, the tensioning member 222 is moved from the second position toward the first position such that the first end 284 of the tensioning member 222 moves toward the base 220.

The first actuator 224 is attached to the tensioning member 222 and is movable in a first direction 303 and a second direction 305. Movement of the actuator 224 results in movement of the tensioning member 222 between its first position and second position. The actuator 224 has a first end 304 and a main body 308 that defines a first actuator passageway 310 and an outside diameter 311. The first actuator passageway 310 has an inside diameter 313. The outside diameter 311 is less than the first inside diameter 239 of the loading member 216 and is equal to about the first outside diameter 295 of the tensioning member 222. The inside diameter 313 is equal to about the first inside diameter 291 of the tensioning member 222. In the illustrated embodiment, the first actuator 224 comprises a linear actuator 325 that can be manually operated or automated.

The inner member 226 is moveable between a first position, as shown in FIG. 15, and a second position, as shown in FIG. 16. The inner member 226 is disposed within the tensioning member passageway 290 in the first position and partially disposed within the tensioning member passageway 290 and the first actuator passageway 310 in the second position. The inner member 226 has a first end 320, a second end 322, and a main body 324 that defines a shoulder 326, a first outside diameter 325, and a second outside diameter 327. The shoulder 326 is disposed between the first end 320 and the second end 322 and interacts with the first shoulder 292 defined by the tensioning member 222 such that a mechanical stop to advancement of the inner member 226 beyond the first shoulder 292 defined by the tensioning member 222 can be achieved. The first outside diameter 325 extends from the second end 322 to the shoulder 326 and is equal to about the first inside diameter 291 of the tensioning member 222. The second outside diameter 327 extends from the shoulder 326 to the first end 320, is less than the first outside diameter 325, and is equal to about the second inside diameter 293 of the tensioning member 222. Optionally, the main body of an inner member (e.g., first inner member 26, second inner member 28, inner member 226) can define one or more recesses, slots, and/or holes to avoid the application of suction on tissue while being processed. For example, the main body of an inner member (e.g., first inner member 26, second inner member 28, inner member 226) can define one or more recesses that extend from the first end of the inner member toward the second end of the inner member, or to the second end of the inner member.

When each of the tensioning member 222 and the inner member 226 is in the first position, the first end 320 (e.g., end surface) of the inner member 226 is disposed on the first hypothetical plane 300, as shown in FIG. 15, that contains the first end 232 (e.g., end surface) of the loading member 216 and the first end 284 (e.g., end surface) of the tensioning member 222. This structural arrangement allows for placement of tissue on the loading member 216, tensioning member 222, and the inner member 226, as described in more detail herein. When the inner member 226 is in the second position, the first end 320 (e.g., end surface) of the inner member 226 is disposed on a third hypothetical plane 342, as shown in FIG. 16, that is disposed within the tensioning member passageway 290 between the first end 232 of the tensioning member 222 and the second end 286 of the tensioning member 222. This structural arrangement allows tissue to sag from the first end 284 of the tensioning member 222 toward the inner member 226, and, depending on the type of tissue and the weight being applied to the tissue, as described in more detail herein, contact the inner member 226.

The second actuator 350 is attached to the second end 322 of the inner member 226 and is movable in a first direction 303 and a second direction 305. Movement of the second actuator 350 results in movement of the inner member 226 between its first position and second position. The second actuator 350 has a first end 352 and a main body 356 that defines an outside diameter 359. The outside diameter 359 is less than the first inside diameter 239 of the loading member 216 and equal to about the first inside diameter 291 of the tensioning member 222. In the illustrated embodiment, the second actuator 350 comprises a linear actuator 351 that can be manually operated or automated. The first and second actuators 224, 350 can optionally be independently moveable, or configured such that they move in unison.

Figure 17:
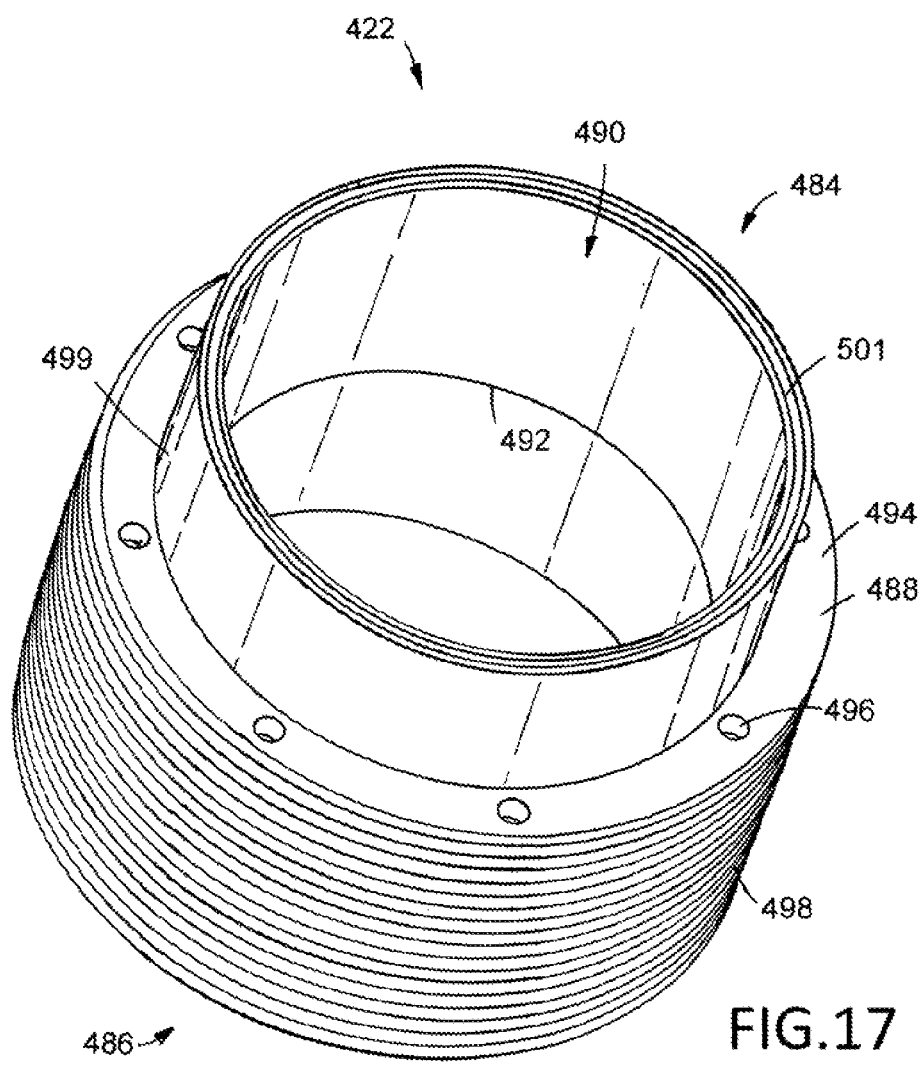
FIG. 17 is a perspective view of an alternative tensioning member.

FIG. 17 illustrates an alternative tensioning member 422 that can used in a material processing apparatus, such as those described herein. The tensioning member 422 is similar to the tensioning member 22 illustrated in FIGS. 1, 2, 3, 4, 5, 6, 7, 8, 9, 10, 11, 12, 13, and 14 and described above, except as detailed below.

In the illustrated embodiment, the tensioning member 422 has a first end 484, a second end 486, and a main body 488 that defines a tensioning member passageway 490, a first shoulder 492, a second shoulder 494, a plurality of guide passageways 496, a thread 498, an outer surface 499, and a recess 501. The recess 501 extends into the main body 488 from the first end 484 toward the second end 486 and is sized and configured to receive a portion of the punch member 610, as described herein. The inclusion of a recess on the first end of a tensioning member assists with cutting tissue subsequent to processing and prevents a punch member from contacting an inner member when cutting tissue, which could result in damage to the first end of the inner member and/or manipulate tissue processing.

Figure 18:
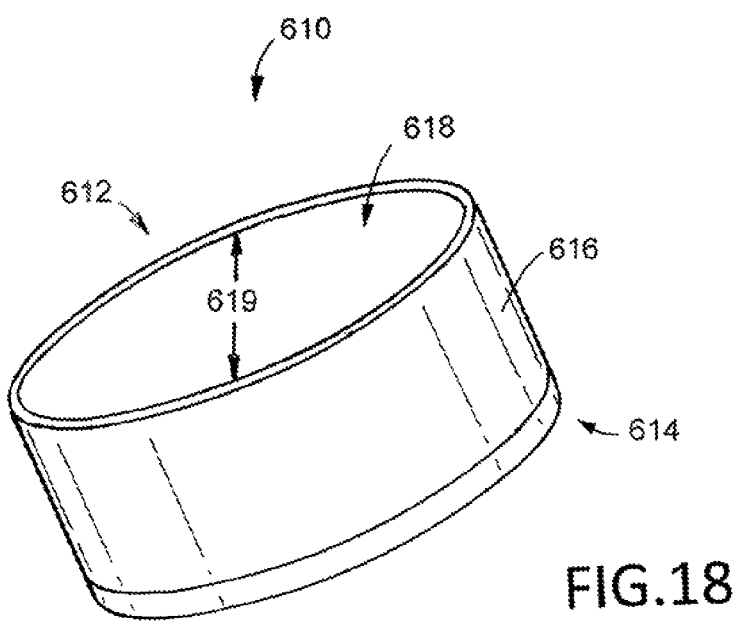
FIG. 18 is a perspective view of an example punch member.
Figure 19:
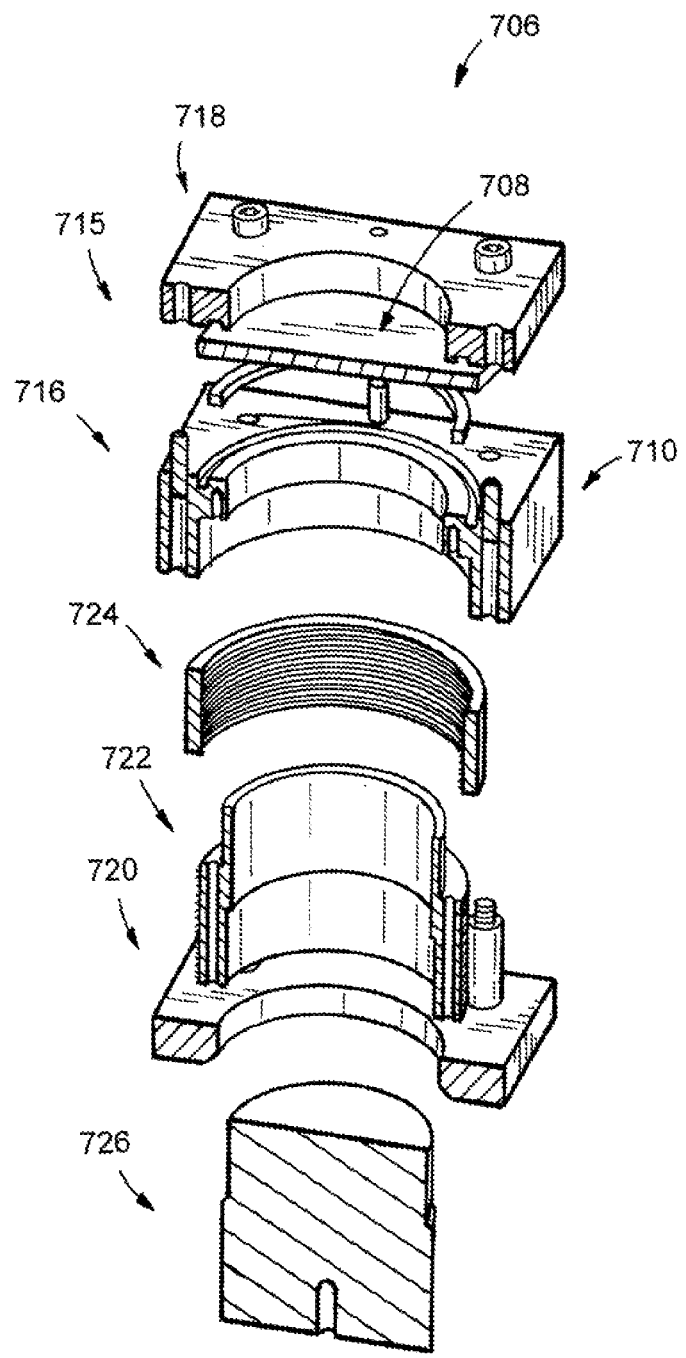
FIG. 19 is an exploded sectional view of an example material processing system taken along a plane that contains the lengthwise axis of the material processing apparatus.
Figure 20:
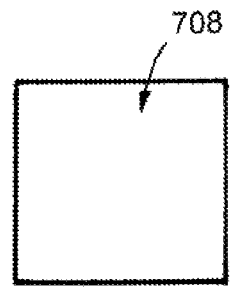
FIG. 20 is a top view of the sheet of tissue used in the material processing system illustrated in FIG. 19.

FIG. 18 illustrates an example punch member 610 that can used to assist with removing tissue from a material processing apparatus, such as those described herein.

The punch member 610 has a first end 612, a sharpened second end 614, and a main body 616 that defines a punch member passageway 618. The punch member passageway 618 extends from the first end 612 to the second end 614 and has an inside diameter 619 that is greater than the second inside diameter of a tensioning member intended to be used with the punch member 610. The sharpened second end 614 of the punch member 610 is configured to engage a first end of a tensioning member (e.g., such that it is disposed within a recess 501 defined by a tensioning member) to cut tissue subsequent to processing. A punch member can be used to maximize the amount of tissue that be removed from a material processing apparatus subsequent to processing.

A punch member can be formed of any suitable material and using any suitable technique or method of manufacture. Selection of a suitable material and of a suitable technique or method of manufacture can be based on various considerations, including the intended use of the punch member. Examples of materials considered suitable to form a punch member include biocompatible materials, materials that can be made biocompatible, metals, such as 316 stainless and 304 stainless, corrosion resistant materials, plastics, polymers, polyethylene, such as high-density polyethylene (HDPE), polypropylene, polycarbonates, silicone, Delrin, transparent materials, opaque materials, combinations of the materials described herein, and any other material considered suitable for a particular embodiment.

While the loading members, the clamping members, the bases, the tensioning members, the actuators, the inner members, and the punch member described herein have been illustrated as having a particular structural arrangement, a loading member, a clamping member, a base, a tensioning member, an actuator, an inner member, and a punch member can have any suitable structural arrangement. Selection of a suitable structural arrangement can be based on various considerations, such as the type of tissue intended to be processed by material processing apparatus.

Figure 21:
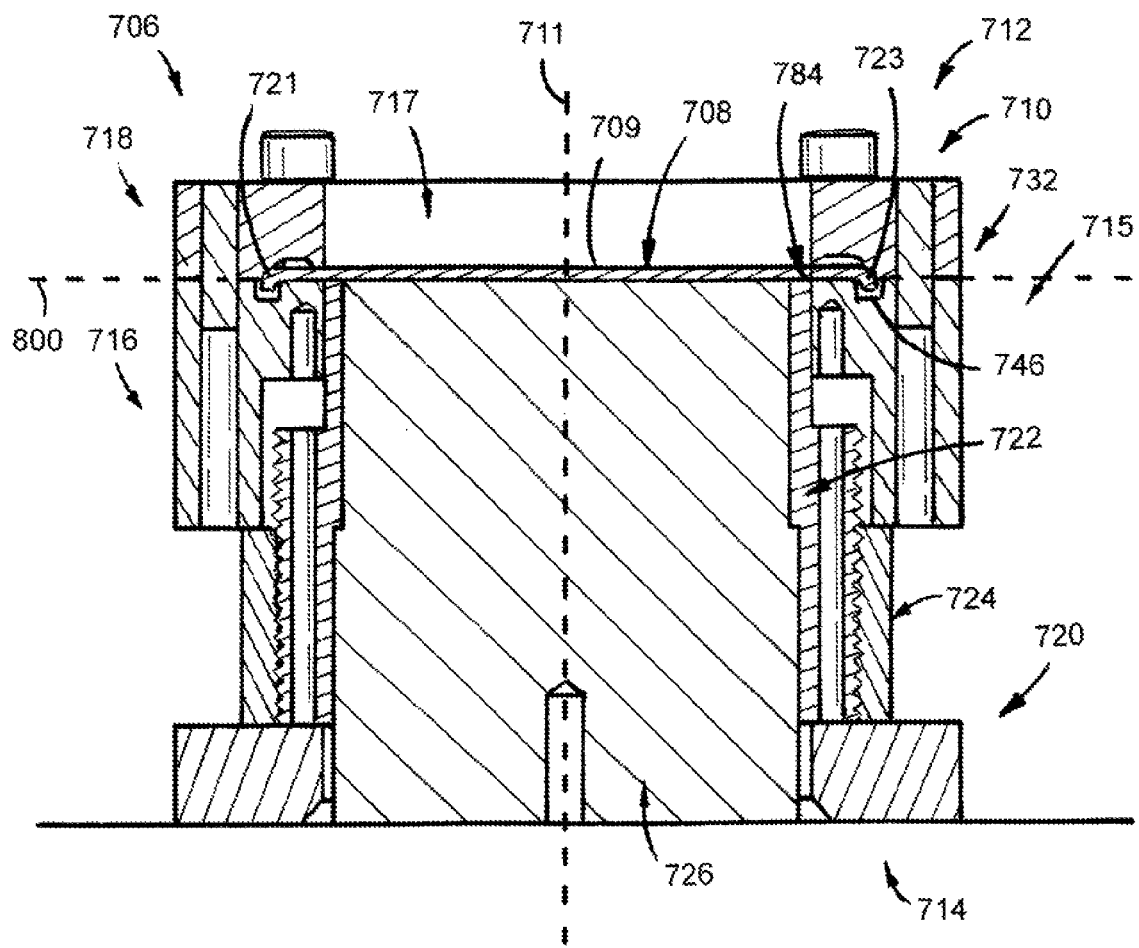
FIG. 21 is a sectional view of the material processing system illustrated in FIG. 19, as assembled, taken along a plane that contains the lengthwise axis of the material processing apparatus. The material processing system is in the loading configuration and includes a first inner member.
Figure 22:
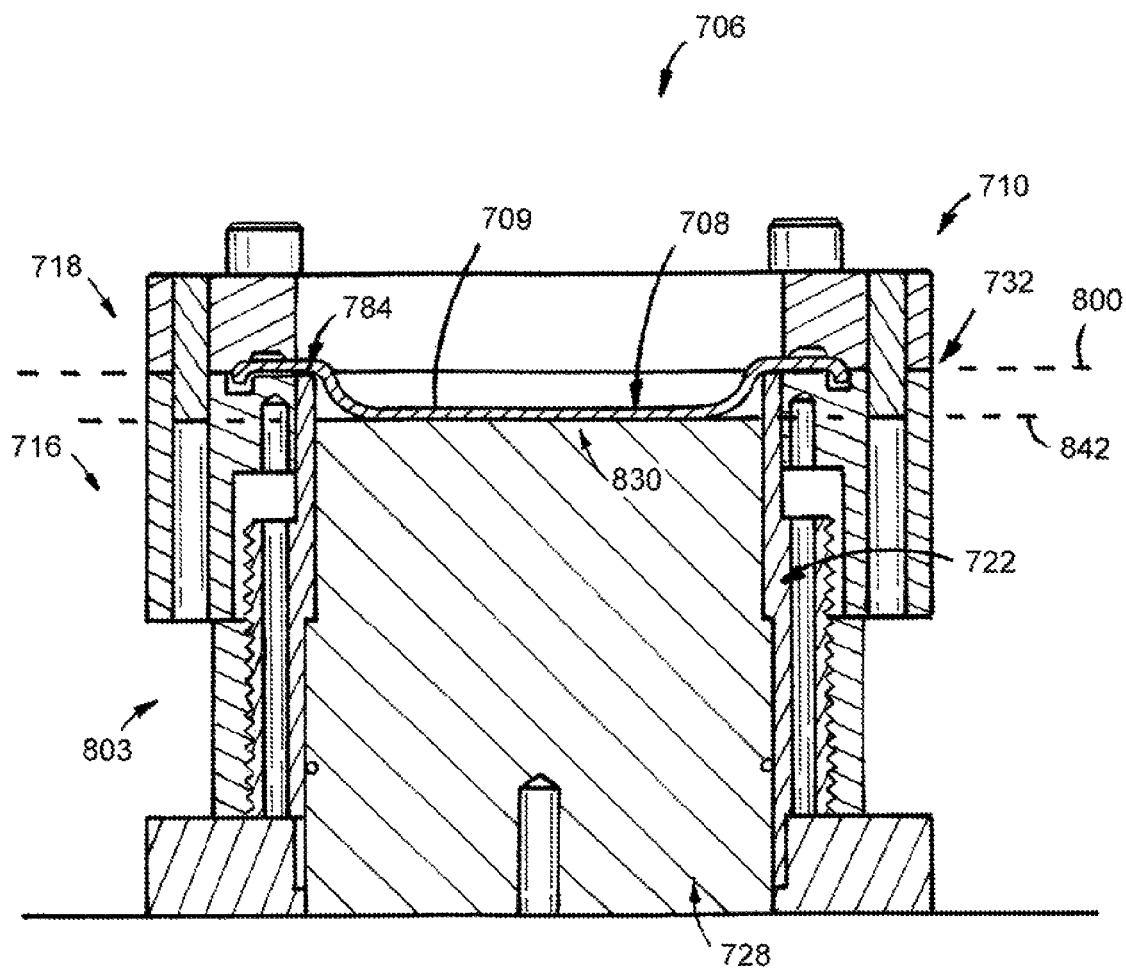
FIG. 22 is another sectional view of the material processing system illustrated in FIG. 19, as assembled, taken along a plane that contains the lengthwise axis of the material processing apparatus. The material processing system includes a second inner member.
Figure 23:
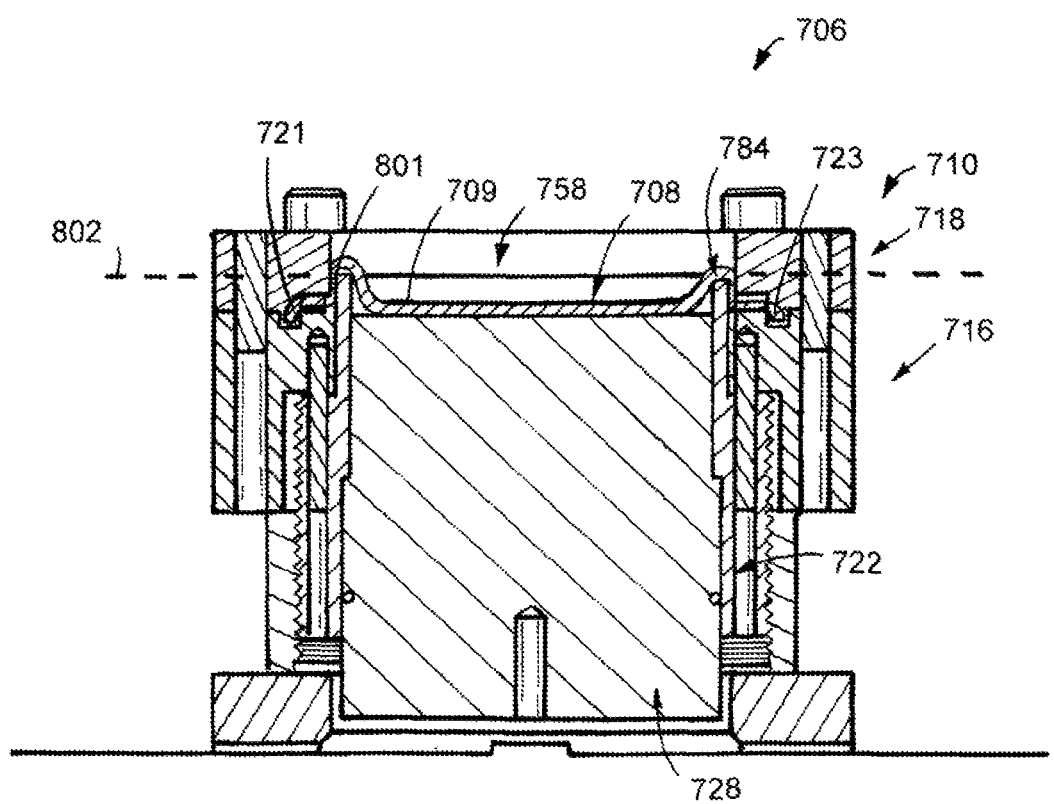
FIG. 23 is another sectional view of the material processing system illustrated in FIG. 19, as assembled, taken along a plane that contains the lengthwise axis of the material processing apparatus. The material processing system is in the tensioning configuration and includes a second inner member.

FIGS. 19, 20, 21, 22, and 23 illustrate an example material processing system 706. The material processing system 706 includes a material processing apparatus 710 similar to the material processing apparatus 10 illustrated in FIGS. 1, 2, 3, 4, 5, 6, 7, 8, 9, 10, 11, 12, 13, and 14 and described above, except as detailed below, and tissue 708 disposed within the material processing apparatus 710. The material processing apparatus 710 has a lengthwise axis 711, a first end 712, a second end 714, and includes a holding member 715, a base 720, a tensioning member 722, an actuator 724, a first inner member 726, and a second inner member 728. The material processing apparatus 210 is moveable between a loading configuration, as shown in FIG. 21, and a tensioning configuration, as shown in FIG. 23.

In the illustrated embodiment, the tissue 708 is disposed within the holding member 715 between the loading member 716 and the clamping member 718 such that the holding member passageway 717 is obstructed by a portion of the tissue 708 that spans the entire cross section of the passageway 717. In the illustrated embodiment, the tissue 708 comprises a single piece, or sheet, of tissue 709.

As shown in FIG. 21, when the material processing apparatus 710 is disposed on a flat surface, includes the first inner member 726, and the tensioning member 722 is in the first position, the first end 784 (e.g., end surface) of the tensioning member 722 is disposed on the first hypothetical plane 800 that contains the first end 732 (e.g., end surface) of the loading member 716. The sheet of tissue 709 is disposed on the tensioning member 722 and the first inner member 726 in this configuration, except for portions 721, 723 that are disposed between the loading member 716 and clamping member 718 and within the recess 746 defined by the loading member 716.

As shown in FIG. 22, when the material processing apparatus 710 is disposed on a flat surface, includes the second inner member 728, and the tensioning member 722 is in the first position, the first end 784 (e.g., end surface) of the tensioning member 722 is disposed on the first hypothetical plane 800 that contains the first end 732 (e.g., end surface) of the loading member 716 and a portion of the sheet of tissue 709 and the first end 830 (e.g., end surface) of the second inner member 728 is disposed on the third hypothetical plane 842. A portion of the sheet of tissue 709 is disposed on the second inner member 728 in this configuration. This structural arrangement allows the tissue 708 to sag from the first end 784 of the tensioning member 722 toward the second inner member 728 and contact the second inner member 728. When the actuator 724 is moved in the first direction 803, the tensioning member 722 is moved from the first position toward the second position such that the first end 784 of the tensioning member 722 moves away from the base 720 and toward the first end 752 of the clamping member 718.

As shown in FIG. 23, when the material processing apparatus 710 is disposed on a flat surface, includes the second inner member 728, and the tensioning member 722 is in the second position, the first end 784 (e.g., end surface) of the tensioning member 722 contacts the tissue and is disposed on the second hypothetical plane 802 that is disposed within the clamping member passageway 758. The sheet of tissue 709 extends from the portions 721, 723 disposed between the loading member 716 and clamping member 718, within the gap 801 defined between the clamping member 718 and the tensioning member 722, over the first end 784 of the tensioning member 722, and toward the second inner member 728. Depending on the type of tissue being processing, the sag defined by the tissue 708 can be natural, or artificially imparted on the tissue by positioning a load on the tissue 708, as described in more detail herein.

While the material processing system 706 has been illustrated as including a sheet of tissue 708, the material processed using a material processing system, such as those described herein, can comprise any suitable material. Selection of a suitable material to process using a material processing system can be based on various considerations, including the intended use of the material subsequent to processing. Examples of suitable materials to process using a material processing system include natural materials, allogeneic materials, xenogeneic materials, synthetic materials, and combinations of natural and synthetic materials. Examples of suitable natural materials include extracellular matrix (ECM) materials, such as small intestine submucosa (SIS), and other bioremodelable materials, such as bovine pericardium. Other examples of suitable ECM materials that can be used include stomach submucosa, liver basement membrane, urinary bladder submucosa, tissue mucosa, and dura mater. Other examples of suitable natural materials include renal capsule matrix, abdominal fascia, parenchyma, such as abdominal parenchyma, connective tissue, pulmonary or lung ligament, tissue laminates, and natural valve leaflets with or without adjacent vessel wall. Pleura is also considered a suitable natural material, including visceral pleura. Examples of suitable synthetic materials include polymeric materials, such as expanded polytetrafluoroethylene, polyurethane, polyurethane urea, polycarbonate, and polyesters.

Figure 24:
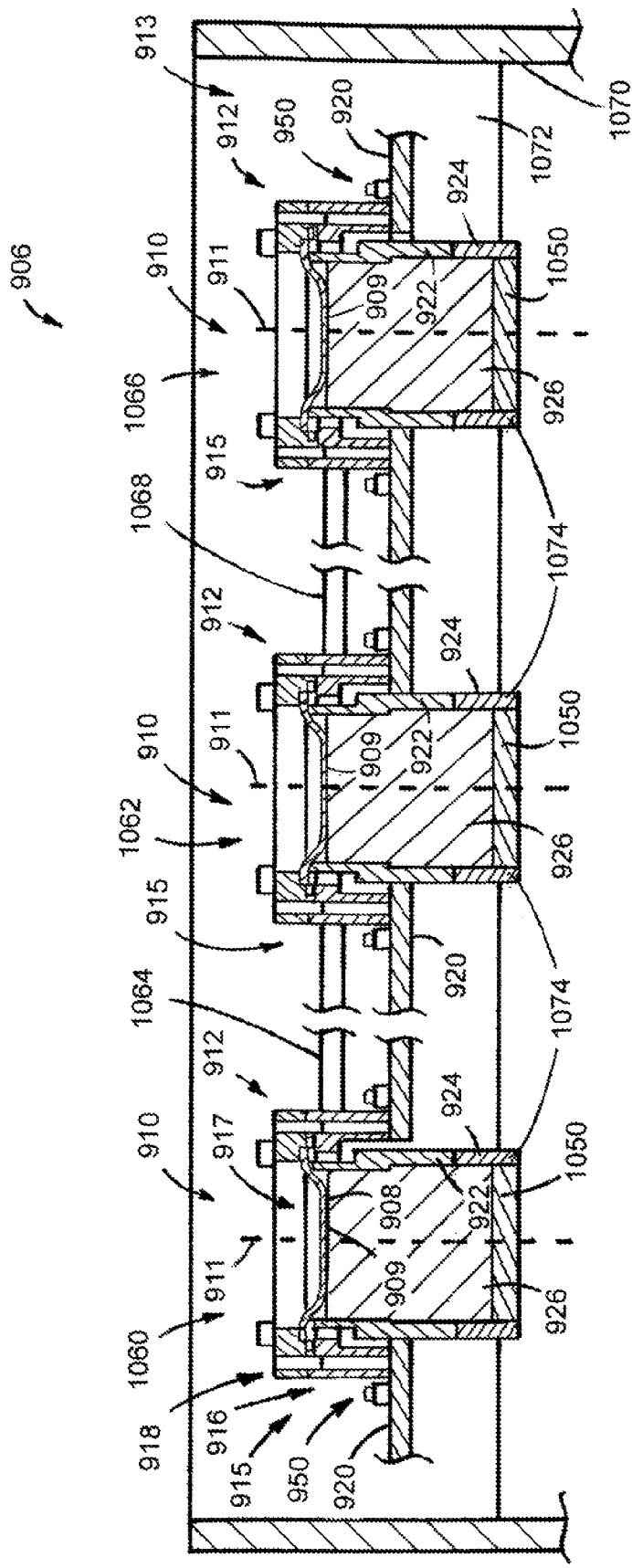
FIG. 24 is a partial sectional view of another example material processing system taken along a plane that contains the lengthwise axis of the material processing apparatus included in the material processing system.

FIG. 24 illustrates another example material processing system 906. The material processing system 906 includes a plurality of material processing apparatus 910, a sheet of tissue 909 disposed within each material processing apparatus 910, and a tank 913. Each material processing system of the plurality of material processing apparatus 910 is similar to the material processing apparatus 210 illustrated in FIGS. 15 and 16 and described above, except as detailed below. Each material processing apparatus of the plurality of material processing apparatus 910 has a lengthwise axis 911, a first end 912, a second end (not shown), and includes a holding member 915, a base 920, a tensioning member 922, a first actuator 924, an inner member 926, and a second actuator 1050.

In the illustrated embodiment, each material processing apparatus of the plurality of material processing apparatus 910 is releasably attached to the base 920 using attachment members 950. A first material processing apparatus 1060 of the plurality of material processing apparatus 910 is attached to a second material processing apparatus 1062 of the plurality of material processing apparatus 910 using a first elongate member 1064. The second material processing apparatus 1062 is attached to a third material processing apparatus 1066 of the plurality of material processing apparatus 910 using a second elongate member 1068.

In the illustrated embodiment, the sheet of tissue 909 disposed within the holding member 915 of each material processing apparatus of the plurality of material processing apparatus 910 is disposed between the loading member 916 and the clamping member 918 such that the holding member passageway 917 is obstructed by a portion of the tissue 908 that spans the entire cross section of the passageway 917.

In the illustrated embodiment, the tank 913 has a main body 1070 that defines a recess 1072 and a plurality of passageways 1074. Each material processing apparatus of the plurality of material processing apparatus 910 is partially disposed within the recess 1072 defined by the tank 913. The first actuator 924 and second actuator 1050 of each material processing apparatus of the plurality of material processing apparatus 910 extends through a passageway of the plurality of passageways 1074.

Various methods of loading tissue into a holding member and methods of processing tissue are described herein. While the methods described herein are shown and described as a series of acts, it is to be understood and appreciated that the methods are not limited by the order of acts, as some acts may in accordance with these methods, occur in the order shown and/or described, in different orders, and/or concurrently with other acts described herein.

Figure 25:
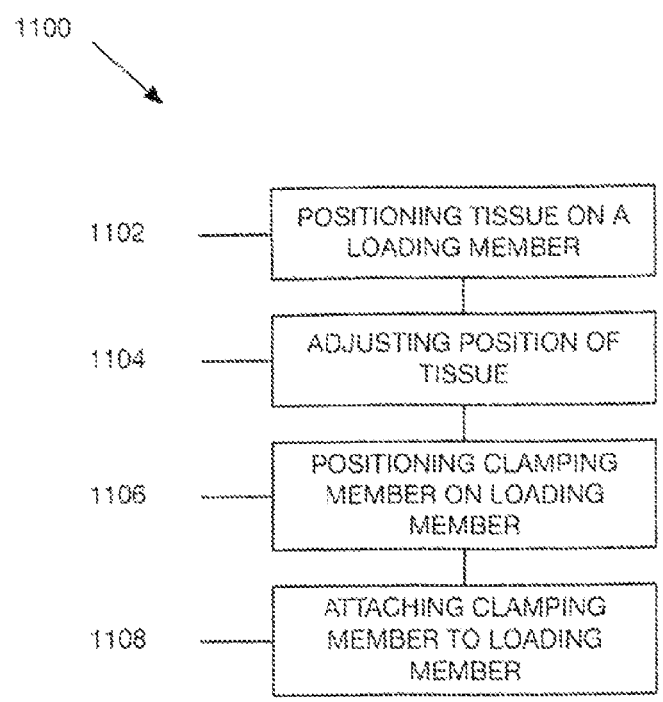
FIG. 25 is a schematic illustration of an example method of loading tissue into a holding member.

FIG. 25 is a schematic illustration of an example method 1100 of loading tissue into a holding member of a material processing apparatus, such as those described herein.

A step 1102 comprises positioning a sheet of tissue on a loading member, a tensioning member, and an inner member such that a portion of the tissue is separated from the loading member, the tensioning member, and the inner member by a fluid layer disposed between the tissue and the loading member, the tensioning member, and the inner member. Another step 1104 comprises adjusting the position of the tissue. Another step 1106 comprises positioning a clamping member on the loading member. Another step 1108 comprises releasably attaching the clamping member to the loading member.

Step 1102 can be accomplished using any suitable loading member, tensioning member, and inner member and selection of a suitable loading member, tensioning member, and inner member can be based on various considerations, including the material that forms a loading member, tensioning member, and inner member. Examples of loading members, tensioning members, and inner members considered suitable to complete a method of loading tissue into a holding member include loading member 16, loading member 216, loading member 716, loading member 916, tensioning member 22, tensioning member 222, tensioning member 722, tensioning member 922, first inner member 26, inner member 226, first inner member 726, inner member 926, and any other loading member, tensioning member, and inner member considered suitable for a particular embodiment.

Step 1102 can be accomplished such that the tissue is positioned on the loading member, tensioning member, and inner member in a resting state. The phrase "resting state" means the tissue is in a state in which the only non-naturally occurring forces being applied to the tissue occur from the tissue's contact with the fluid layer, the loading member, the tensioning member, and/or the inner member when the tissue is positioned on the fluid layer, the loading member, the tensioning member, and the inner member, occur from the tissue's contact with the fluid layer when the tissue is positioned on the fluid layer, and/or occur from the tissue's contact with the loading member, tensioning member, and inner member when the tissue is positioned on the loading member, tensioning member, and inner member. A resting state may include a state in which a sheet of tissue includes wrinkles and/or folds, a state in which a sheet of tissue is planar (e.g., a planar resting state) in which a surface of the tissue (e.g., top surface, bottom surface) is parallel, or substantially parallel, to a surface of a loading member (e.g., a surface of the loading member on which the tissue is intended to be disposed), a surface of a tensioning member (e.g., a surface of the tensioning member on which the tissue is intended to be disposed), and/or surface of an inner member (e.g., a surface of the inner member on which the tissue is intended to be disposed), a resting state in which a surface of the tissue is similar, or substantially similar, to a surface of a loading member, tensioning member, and/or inner member (e.g., a curved surface of the loading member, tensioning member, and/or inner member on which the tissue is intended to be disposed), and any other state considered suitable for a particular embodiment. Depending on the material that forms a loading member, tensioning member, and/or inner member (e.g., low-friction materials, such as Teflon), in alternative embodiments step 1102 can comprise positioning a sheet of tissue on a loading member, tensioning member, and inner member such that the tissue contacts the loading member, tensioning member, and inner member.

Step 1102 can be accomplished using any suitable technique or method of positioning tissue on a loading member, tensioning member, and inner member and selection of a suitable technique or method can be based on various considerations, including the structural arrangement of a loading member, tensioning member, and inner member. Examples of techniques and methods considered suitable include using the hands of an individual, using automated robotics systems, convention tools, such as hand tools, and any other technique or method considered suitable for a particular embodiment. Depending on the structural arrangement of a loading member, tensioning member, and inner member, in alternative embodiments, step 1102 can comprise positioning a sheet of tissue on a loading member and an inner member such that a portion of the tissue is separated from the loading member and the inner member by a fluid layer disposed between the tissue, the loading member, and the inner member.

Figure 26:
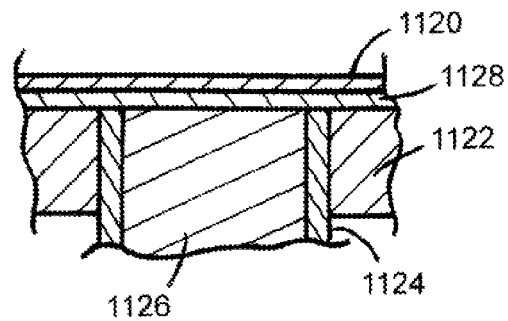
FIG. 26 is a partial sectional view of a sheet of tissue positioned on a loading member.

A fluid layer disposed between tissue and a loading member, tensioning member, and inner member can include any suitable fluid positioned between the tissue and the loading member, tensioning member, and inner member using any suitable technique or method. Selection of a suitable fluid and technique or method to position the fluid layer between tissue and a loading member, a tensioning member, and an inner member can be based on various considerations, including the type of tissue being positioned within a holding member. Examples of fluids considered suitable to position between tissue and a loading member, tensioning member, and inner member include lubricious coatings, such as those that are applied to the loading member prior to step 1102, saline, phosphate buffered saline, lactated ringers, fluids described herein, such as fixation solutions, water, neutral oils, and any other fluid considered suitable for a particular embodiment. Examples of suitable techniques and methods of positioning a fluid layer between tissue and a loading member, tensioning member, and inner member include applying a fluid layer prior to, during, and/or subsequent to, step 1102, applying fluid to the loading member, tensioning member, and inner member using an applicator, placing a loading member, tensioning member, and inner member within a fluid bath such that a top surface of the loading member, tensioning member, and inner member is disposed at, near, or below, the level of the fluid within the bath, and any other technique or method considered suitable for a particular embodiment. An optional step that can be completed prior to step 1102 comprises applying a fluid to the loading member, tensioning member, and inner member to create a fluid layer. FIG. 26 illustrates a sheet of tissue 1120 positioned on a loading member 1122, tensioning member 1124, and inner member 1126 such that the tissue 1120 is in its resting state and a portion of the tissue 1120 is separated from the loading member 1122, tensioning member 1124, and inner member 1126 by a fluid layer 1128 disposed between the tissue 1120 and the loading member 1122, tensioning member 1124, and inner member 1126.

While step 1102 has been described as being accomplished by positioning a sheet of tissue, tissue having any suitable configuration can be positioned on a loading member in a method of loading tissue into a holding member. While step 1102 has been described as being accomplished such that a portion of the tissue is separated from the loading member, tensioning member, and inner member by a fluid layer disposed between the tissue and the loading member, tensioning member, and inner member, any suitable amount of tissue can be separated from a loading member, tensioning member, and inner member by a fluid layer disposed between the tissue and the loading member. Examples of suitable amounts of tissue include an entire sheet of tissue, a majority of a sheet of tissue, more than half of a sheet of tissue, more than one quarter of a sheet of tissue, less than one quarter of a sheet of tissue, and any other amount of tissue considered suitable for a particular embodiment.

Step 1104 can be accomplished using any suitable technique or method of adjusting a position of the tissue and selection of a suitable technique or method can be based on various considerations, including the type of tissue being positioned within a holding member. Examples of techniques and methods considered suitable include using forceps, the hands of an individual, conventional tools, robotic systems, and any other technique or method considered suitable for a particular embodiment. Step 1104 is accomplished to remove any wrinkles in the tissue and/or to position the tissue such that it lays flat on the loading member and/or any other component.

Step 1106 can be accomplished using any suitable technique or method of positioning a clamping member on a loading member and selection of a suitable technique or method can be based on various considerations, including the structural arrangement of a clamping member and/or loading member. Examples of techniques and methods considered suitable include using the hands of an individual, using automated robotics systems, convention tools, such as hand tools, and any other technique or method considered suitable for a particular embodiment. It is considered advantageous to complete step 1106 such that the position of a loading member relative to a clamping member is maintained along two axes (e.g., an x-axis and a y-axis) to reduce, or eliminate, any unintentional deformation and/or stress imparted on tissue positioned between a loading member and a clamping member during positioning of a clamping member relative a loading member and/or attachment of a clamping member to a loading member.

Step 1108 can be accomplished using any suitable technique or method of releasably attaching a clamping member to a loading member and selection of a suitable technique or method can be based on various considerations, including the structural arrangement of a clamping member and/or loading member. Examples of techniques and methods considered suitable include using threaded connections, snap fit attachments, using one or more connectors, one or more mating slots and projections, one or more sealed unions, tapered attachments, external clamps, pneumatic clamping mechanisms, adhesives, and any other technique or method of attachment considered suitable for a particular embodiment.

Figure 27:
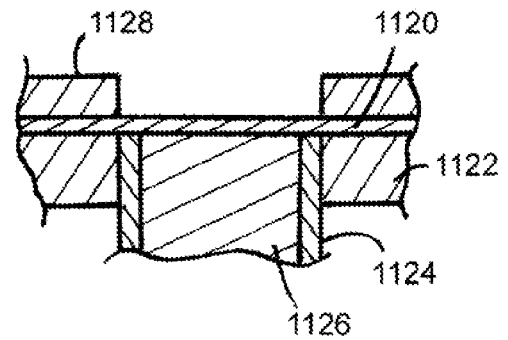
FIG. 27 is a partial sectional view of a sheet of tissue positioned between a clamping member and a loading member.

Step 1108 can be accomplished such that the tissue is in the clamped state. The phrase "clamped state" means the tissue is in a state in which forces are applied on the tissue by the clamping member and the loading member such that the portion of the tissue contacts the clamping member and the loading member. For example, a clamped state can include contact between a gripping member of a clamping member and the tissue such that the gripping member maintains the position of the tissue during use. FIG. 27 illustrates a sheet of tissue 1120 positioned on a loading member 1122, a tensioning member 1124, and an inner member 1126 such that the tissue 1120 is in its clamped state and a portion of the tissue 1120 contacts the clamping member 1128, the loading member 1122, the tensioning member 1124, and the inner member 1126.

While various steps, alternative steps, and optional steps have been described above with respect to the example method 1100, these steps, alternative steps, and optional steps can be included in, accomplished concurrently with, and/or accomplished in the alternative to, the method, steps, alternative steps, and/or optional steps described herein with respect to example method 1200.

Figure 28:
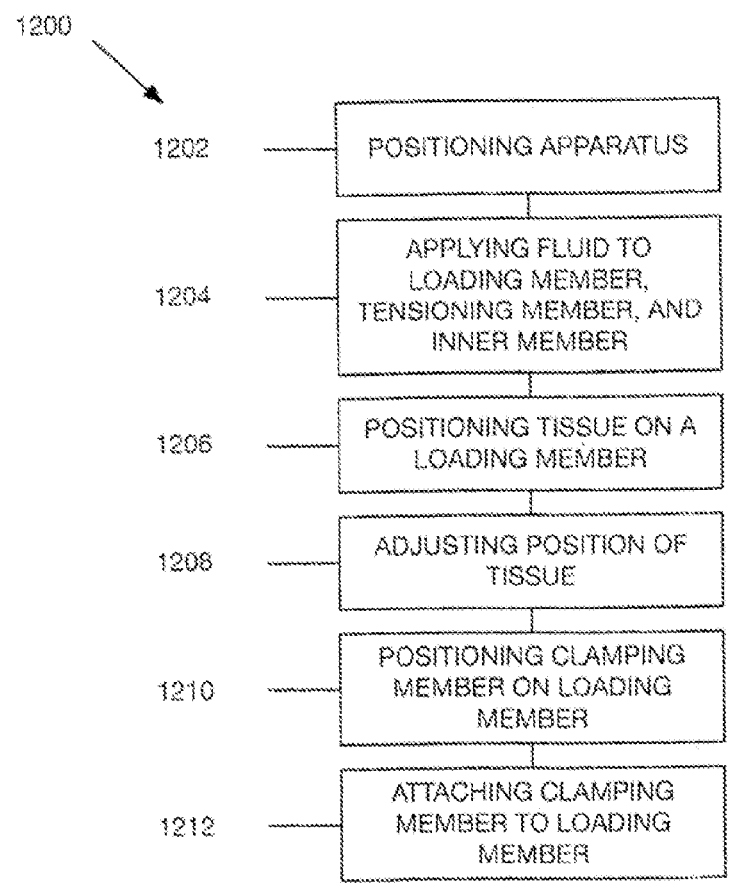
FIG. 28 is a schematic illustration of another example method of loading tissue into a holding member.

FIG. 28 is a schematic illustration of another example method 1200 of loading tissue into a holding member of a material processing apparatus, such as those described herein.

A step 1202 comprises positioning a material processing apparatus such that the first end of the loading member, the first end of the tensioning member, and the first end of the inner member are disposed on a first hypothetical plane. Another step 1204 comprises applying a fluid to the loading member, the tensioning member, and the inner member. Another step 1206 comprises positioning a sheet of tissue on the loading member, the tensioning member, and the inner member such that the tissue is in its resting state and a portion of the tissue is separated from the loading member, the tensioning member, and the inner member by a fluid layer disposed between the tissue and the loading member, the tensioning member, and the inner member. Another step 1208 comprises adjusting the position of the tissue. Another step 1210 comprises positioning a clamping member on the loading member. Another step 1212 comprises releasably attaching the clamping member to the loading member such that the tissue is in the clamped state.

In embodiments in which material processing apparatus 10 is being used to complete method 1200, step 1202 can comprise positioning the loading member 16, the tensioning member 22, and the first inner member 26 on a flat surface with a guide member of the loading member 16 directed away from the surface. In embodiments in which material processing apparatus 210 is being used to complete method 1200, step 1202 can comprise positioning the tensioning member 222 in the first position and positioning the inner member 226 in the first position.

Step 1204 can be accomplished using any suitable technique or method of applying any suitable fluid to a loading member and a fluid can be applied to any suitable portion of a loading member, a tensioning member, and an inner member. Examples of techniques and methods of applying a fluid to a loading member, a tensioning member, and an inner member considered suitable include applying a fluid layer prior to, during, and/or subsequent to, step 1202, applying fluid to a loading member, a tensioning member, and an inner member using an applicator, placing a loading member, a tensioning member, and an inner member within a fluid bath such that a top surface of the loading member, a tensioning member, and an inner member is disposed at, near, or below, the level of the fluid within the bath, and/or any other technique or method considered suitable for a particular embodiment. Examples of fluids considered suitable to apply to loading member, a tensioning member, and an inner member include lubricious coatings, saline, phosphate buffered saline, those described herein, and any other fluid considered suitable for a particular embodiment. Optionally, step 1204 can be omitted from method 1200 in embodiments in which a fluid (e.g., lubricious coating) has already been applied to a loading member, a tensioning member, and an inner member or in embodiments in which a loading member, a tensioning member, and an inner member is formed of a non-stick material.

Step 1206 can be accomplished by positioning a single sheet of tissue over the loading member passageway. The sheet can be precut such that when it is disposed on a loading member the sheet does not extend over a guide member and/or an attachment passageway.

Step 1208 can be accomplished as described above with respect to step 1104. Step 1208 can be accomplished such that all wrinkles are removed from the tissue and/or the tissue is centered on the loading member passageway. An optional step comprises trimming the tissue in embodiments in which the tissue obstructs or contacts any guide member and/or obstructs or contacts any attachment passageways used to releasably attach a loading member to a clamping member. Another optional step comprises applying fluid to the tissue subsequent to being positioned on a loading member, a tensioning member, and an inner member. Another optional step comprises confirming that the tissue is large enough to contact the gripping member of a holding member (e.g., gripping member of clamping member).

Step 1210 can be accomplished as described above with respect to step 1106.

Step 1212 can be accomplished as described above with respect to step 1108.

While various steps, alternative steps, and optional steps have been described above with respect to the example method 1200, these steps, alternative steps, and optional steps can be included in, accomplished concurrently with, and/or accomplished in the alternative to, the method, steps, alternative steps, and/or optional steps described herein with respect to example method 1100.

Figure 29:
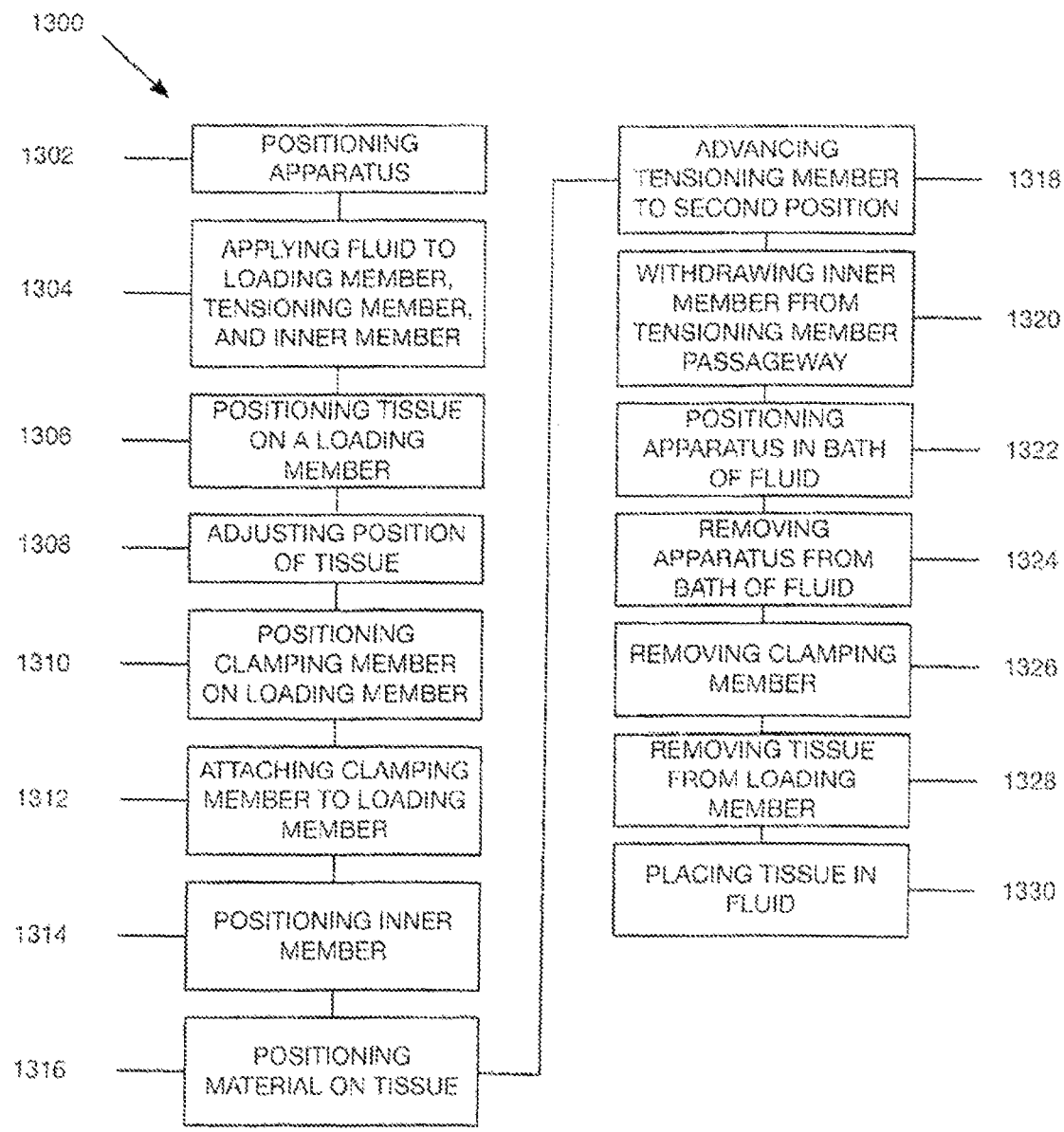
FIG. 29 is a schematic illustration of an example method of processing tissue.

FIG. 29 is a schematic illustration of an example method 1300 of processing tissue.

A step 1302 comprises positioning a material processing apparatus such that the first end of the loading member, the first end of the tensioning member, and the first end of the inner member are disposed on a first hypothetical plane. Another step 1304 comprises applying a fluid to the loading member, the tensioning member, and the first inner member. Another step 1306 comprises positioning a sheet of tissue on the loading member, the tensioning member, and the first inner member such that the tissue is in its resting state and a portion of the tissue is separated from the loading member, the tensioning member, and the first inner member by a fluid layer disposed between the tissue and the loading member, the tensioning member, and the first inner member. Another step 1308 comprises adjusting the position of the tissue. Another step 1310 comprises positioning a clamping member on the loading member. Another step 1312 comprises releasably attaching the clamping member to the loading member such that the tissue is in the clamped state. Another step 1314 comprises positioning the inner member such that the first end of the inner member is positioned on a second hypothetical plane that is disposed within the tensioning member passageway. Another step 1316 comprises positioning a material on the tissue such that the tissue sags and contacts the inner member. Another step 1318 comprises advancing the tensioning member to its second position. Another step 1320 comprises withdrawing the inner member from the tensioning member passageway. Another step 1322 comprises positioning the material processing apparatus in a bath of fluid for a period of time. Another step 1324 comprises removing the material processing apparatus from the bath of fluid. Another step 1326 comprises removing the clamping member from the loading member. Another step 1328 comprises removing the tissue from the loading member. Another step 1330 comprises placing the tissue in a fluid for a period of time.

Step 1302 can be accomplished as described above with respect to step 1202. Depending on the structural arrangement of a material processing apparatus, an optional step that can be completed prior to step 1302 comprises moving a tensioning member to its first position. Another optional step comprises moving an inner member to its first position. In embodiments in which material processing apparatus 10 is being used to process tissue, an initial step can include introducing the first inner member into the tensioning member passageway. Another optional step that can be completed in embodiments in which material processing apparatus 10 is being used to process tissue comprises positioning the material processing apparatus on a flat surface (e.g., such that the second end of the first inner member, the second end of the tensioning member, and the second end of the base are disposed on the surface). Another optional step comprises removing the clamping member from the loading member.

Step 1304 can be accomplished as described above with respect to step 1204. Step 1306 can be accomplished as described above with respect to step 1206. Step 1308 can be accomplished as described above with respect to step 1208. Step 1310 can be accomplished as described above with respect to step 1210. Step 1312 can be accomplished as described above with respect to step 1212.

In embodiments in which material processing apparatus 10 is being used to process tissue, step 1314 comprises the following steps: removing the material processing apparatus from the surface on which it is disposed; removing the first inner member from the tensioning member passageway; introducing the second inner member into the tensioning member passageway; and positioning the second end of the loading member, the second end of the tensioning member, and the second end of the second inner member on a flat surface. In embodiments in which material processing apparatus 210 is being used to process tissue, step 1314 can be accomplished by advancing the inner member away from the first end of the loading member and to its second position by activating the second actuator.

Step 1316 can be accomplished by positioning any suitable material and any suitable amount of material on the tissue (e.g., first surface of the tissue) such that the tissue sags and contacts (e.g., the second surface of the tissue) the inner member (e.g., second inner member in embodiments in which material processing apparatus 10 is being used to process tissue). Examples of materials considered suitable to position on tissue include liquids, such as phosphate buffered saline, water, spherical ball bearings (e.g., stainless steel, polypropylene), and any other material considered suitable for a particular embodiment. Examples of suitable amounts of material considered suitable to position on tissue include an amount of material capable of deforming the tissue along an axis that extends through the tissue and is parallel, or coaxial with, a lengthwise axis of a material processing apparatus. Examples of amounts of deformation considered suitable to impart on tissue include deformations that are equal to, less than, greater than, or about 5 millimeters, 6 millimeters, 7 millimeters, 8 millimeters, 9 millimeters, 10 millimeters, between about 2 millimeters and about 20 millimeters of deformation, between about 5 millimeters and about 10 millimeters of deformation, and any other suitable amount of deformation considered suitable for a particular embodiment. The amount of deformation imparted on tissue when a material is disposed on the tissue is dependent upon the mechanical properties of the tissue and the thickness of the tissue being processed.

In embodiments in which material processing apparatus 10 is being used to process tissue, step 1318 can be accomplished by rotating the actuator in the first direction such that the tensioning member moves toward its second position. The second inner member moves in conjunction with the tensioning member such that the first end of the tensioning member and the first end of the second inner member are disposed from one another the same distance as the tensioning member travels from its first position to its second position. In embodiments in which material processing apparatus 210 is being used to process tissue, step 1318 can be accomplished by activating the first actuator. The inner member moves in conjunction with the tensioning member such that the first end of the tensioning member and the first end of the second inner member are disposed from one another the same distance as the tensioning member travels from its first position to its second position. This can be accomplished using both the first and second actuators. An optional step comprises engaging a locking mechanism such that the tensioning member and actuator are releasably fixed relative to one another. Completion of step 1318 increases the tension being applied on the tissue and reduces the amount of tissue that contacts the inner member (e.g., second inner member in embodiments in which material processing apparatus 10 is being used to process tissue). An optional step comprises continuing advancement of the first end of the tensioning member away from the loading member until the tissue breaks contact with the inner member (e.g., second inner member in embodiments in which material processing apparatus 10 is being used to process tissue). This optional step can be accomplished by directly visualizing the tissue and the first end of the inner member (e.g., through transparent materials), using a load sensor, feedback loop, or any other technique or method considered suitable for a particular embodiment. Optionally, these technique and methods can be utilized to adjust the position of a tensioning member and/or inner member. Another optional step comprises continuing advancement of the first end of the first end of the tensioning member away from the loading member until a desired amount of tension is applied to the tissue. Another optional step comprises adjusting the position of the first end of the inner member. This optional step can be accomplished using any suitable technique or method, such as those described herein.

In an alternative embodiment, step 1314, step 1316, and step 1318 can be omitted from method 1300 and the following steps can be completed in the following order, or any other order considered suitable for a particular embodiment: advancing the tensioning member to its second position, positioning a material on the tissue such that the tissue sags, and advancing the tensioning member toward its first position until the tissue contacts the inner member. The optional step of advancing the tensioning member toward its first position until the tissue contacts the inner member can be accomplished by directly visualizing the tissue and the first end of the inner member (e.g., through transparent materials), using a load sensor, feedback loop, or any other technique or method considered suitable for a particular embodiment.

In another alternative embodiment in which the tissue is substantially uniform with a low variability in mechanical properties, step 1314, step 1316, and step 1318 can be omitted from method 1300 and the following steps can be completed in the following order, or any other order considered suitable for a particular embodiment: advancing the tensioning member to its second position. This alternative embodiment provides a mechanism for uniformly tensioning tissue without having to position a material on the tissue. This alternative method can be completed on any suitable tissue, such as tissue that has a limited amount of variability in mechanical properties throughout the tissue.

In embodiments in which material processing apparatus 10 is being used to process tissue, step 1320 can be accomplished by withdrawing the second inner member from the tensioning member passageway. In embodiments in which material processing apparatus 210 is being used to process tissue, this step can be accomplished by activating the second actuator such that the inner member is withdrawn from the tensioning member passageway.

Step 1322 can be accomplished by positioning the material processing apparatus in any suitable fluid for any suitable period of time. Examples of suitable fluids include chemical fixatives, such as aldehydes, e.g., formaldehyde, glutaraldehyde, and formalin, and carbodiimides, such as ethyl dimethylaminopropyl carbodiimide, dicyclohexylcarbodiimide, solutions, storage solutions, tanning agents, tanning agents in a buffering solution, and any other fluid considered suitable for a particular embodiment. Examples of suitable period of time include one or more minutes, hours, days, weeks, months, and any other period of time considered suitable for a particular embodiment. An optional step comprises positioning the material processing apparatus in the fluid bath such that the tissue is vertical. This optional step provides a mechanism for removing any air trapped within the tensioning member passageway (e.g., under the tissue, adjacent the second surface of the tissue). In embodiments in which material processing apparatus 210 is being used to process tissue, step 1322 can be accomplished by filling the recess within which the apparatus is disposed with a fluid.

An optional step that can be completed prior to, or subsequent to, step 1324 comprises determining the characteristics of the tissue. This optional step can be accomplished using an ultrasound transducer in communication with one, or both, of the portion of the tensioning member passageway disposed between the tissue and the first end of the clamping member and/or the portion of the tensioning member passageway disposed between the tissue and the second end of the tensioning member. For example, any material processing apparatus described herein can include one or more ultrasound transducers in communication with a portion of a tensioning member passageway. Any suitable ultrasound transducer can be included in a material processing apparatus and selection of a suitable ultrasound transducer can be based on various considerations, including the type of tissue being processed. Examples of ultrasound transducers considered suitable to include in a material processing apparatus include linear arrays, phased arrays, single element transducers with frequency ranges between about 20 kHz and about 100 MHz, a matrix of transducers, high-frequency transducers, multiple-frequency transducers, movable transducers, transducers disposed parallel, and/or perpendicular to, a tissue being processed, combinations of those described herein, and any other transducer considered suitable for a particular embodiment. For example, an array of transducers could be utilized to create a full x-y patterning of tissue characteristics. Alternative to, or in combination with use of an ultrasound transducer, optical measuring devices and/or laser measuring devices could be utilized to characterize tissue being processed.

An optional step that can be completed prior to, or subsequent to, step 1324 comprises removing the fluid within the bath. An optional step that can be completed subsequent to step 1324 comprises introducing the inner member into the tensioning member passageway. In embodiments in which material processing apparatus 10 is being used to process tissue, this optional step can be accomplished by introducing the first inner member into the tensioning member passageway such that it is in its first position.

Step 1326 can be accomplished using any suitable technique or method of removing a clamping member from a loading member and selection of a suitable technique or method can be based on various considerations, including the structural arrangement of a clamping member and/or loading member. Examples of techniques and methods considered suitable include using the hands of an individual, using automated robotics systems, convention tools, such as hand tools, and any other technique or method considered suitable for a particular embodiment. It is considered advantageous to complete step 1326 such that the position of a loading member relative to a clamping member is maintained along an x-axis and a y-axis to reduce, or eliminate, any unintentional deformation and/or stress imparted on tissue positioned between a loading member and a clamping member.

Step 1328 can be accomplished using any suitable technique or method of removing tissue from a loading member and selection of a suitable technique or method can be based on various considerations, including the structural arrangement of a loading member. Examples of techniques and methods considered suitable include using the hands of an individual, using automated robotics systems, convention tools, such as hand tools, and any other technique or method considered suitable for a particular embodiment. In an alternative embodiment, step 1326 can be omitted from method 1300 and step 1328 could be accomplished by using the punch member 610 to detach the tissue without removing a clamping member. This alternative step would complete any desired trimming while concurrently removing the tissue from a loading member.

An optional step that can be completed prior to, or subsequent to, step 1328 comprises trimming the tissue into a desired geometry (e.g., circular). For example, in some embodiments, the portion of tissue disposed between the clamping member and the loading member (e.g., adjacent an O-ring) will not have desired properties and can be discarded. Another optional step that can be completed prior to, or subsequent to, step 1328 comprises marking the orientation of the tissue.

Step 1330 can be accomplished by placing the tissue in any suitable fluid for any period of time. Examples of suitable fluids include chemical fixatives, such as aldehydes, e.g., formaldehyde, glutaraldehyde, and formalin, and carbodiimides, such as ethyl dimethylaminopropyl carbodiimide, dicyclohexylcarbodiimide, solutions, storage solutions, tanning agents, tanning agents in a buffering solution, and any other fluid considered suitable for a particular embodiment. Examples of suitable period of time include one or more minutes, hours, days, weeks, months, and any other period of time considered suitable for a particular embodiment. For example, the tissue can be placed within a fixation solution for twenty hours.

An optional step that can be completed subsequent to step 1330 comprises placing the tissue in a storage solution and storing at about 4° C. Optionally, the tissue can be stored in a sterilized package. Alternative embodiments, however, could store the tissue at other temperatures, such as those equal to, greater than, less than, or about 3° C., 4° C., 5° C., and any other temperature considered suitable for a particular embodiment.

Any of the materials described herein (e.g., tissue) can be processed using the apparatus, systems, methods, steps, alternative steps, and/or optional steps described herein to produce a product, such as a tissue product, that is processed using a material processing apparatus. For example, a sheet of tissue that is produced using a material processing apparatus described herein and/or using one or more of the methods, steps, alternative steps, and/or optional steps described herein can be claimed.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A material processing apparatus comprising:
    a holding member defining a holding member passageway having an inside diameter;
    a base attached to the holding member and defining a base passageway;
    a tensioning member partially disposed within the holding member passageway, the tensioning member having a first end, a second end, an outside diameter, and a main body defining a tensioning member passageway, the tensioning member moveable relative to the holding member between a first position and a second position, the outside diameter being less than the inside diameter of the holding member, the tensioning member passageway extending from first end to the second end;
    an actuator attached to the tensioning member and moveable in a first direction and a second direction, movement of the actuator resulting in movement of the tensioning member between its first position and second position; and
    an inner member adapted to be disposed within the tensioning member passageway.

2. The material processing apparatus of claim 1, wherein the holding member comprises a loading member and a clamping member, the loading member defining a loading member passageway having an inside diameter, the clamping member releasably attached to the loading member and defining a clamping member passageway having an inside diameter that is greater than the inside diameter of the loading member passageway, the loading member passageway and the clamping member passageway cooperatively defining the holding member passageway.

3. The material processing apparatus of claim 2, wherein the loading member has a first end; and
    wherein the first end of the tensioning member is disposed on a first hypothetical plane containing the first end of the loading member when the tensioning member is in the first position.

4. The material processing apparatus of claim 3, wherein the first end of the tensioning member is disposed on a second hypothetical plane disposed within the clamping member passageway when the tensioning member is in the second position.

5. The material processing apparatus of claim 3, wherein the inner member has a first end disposed on the first hypothetical plane when disposed within the tensioning member passageway.

6. The material processing apparatus of claim 2, wherein the loading member has a first end; and
    wherein the first end of the tensioning member is disposed on a first hypothetical plane disposed near the first end of the loading member when the tensioning member is in the first position.

7. The material processing apparatus of claim 6, wherein the first end of the tensioning member is disposed on a second hypothetical plane disposed within the clamping member passageway when the tensioning member is in the second position.

8. The material processing apparatus of claim 6, wherein the inner member has a first end disposed near the first hypothetical plane when disposed within the tensioning member passageway.

9. The material processing apparatus of claim 2, further comprising a gripping member disposed between the loading member and the clamping member.

10. The material processing apparatus of claim 2, wherein the loading member includes a first guide member and the clamping member includes a second guide member that mates with the first guide member to prevent movement of the loading member relative to the clamping member along two axes during releasable attachment of the clamping member to the loading member.

11. The material processing apparatus of claim 10, wherein the first guide member comprises a plurality of guide pins and the second guide member comprises a plurality of guide holes.

12. The material processing apparatus of claim 2, wherein the loading member defines a guide recess;
    wherein the tensioning member defines a guide passageway that is coaxial with the guide recess; and
    further comprising a pin disposed within the guide recess and the guide passageway.

13. The material processing apparatus of claim 1, further comprising a second inner member adapted to be disposed within the tensioning member passageway, the second inner member having a first end disposed on a second hypothetical plane disposed within the tensioning member passageway when disposed within the tensioning member passageway.

14. The material processing apparatus of claim 1, wherein the tensioning member is disposed on the base in the first position.

15. The material processing apparatus of claim 1, wherein the actuator is disposed on the base.

16. The material processing apparatus of claim 1, wherein the holding member is disposed on the actuator.

17. The material processing apparatus of claim 1, wherein the base is releasably attached to the holding member.

18. The material processing apparatus of claim 1, wherein the actuator is rotatably attached to the tensioning member.

19. The material processing apparatus of claim 1, wherein the actuator is a linear actuator.

20. The material processing apparatus of claim 1, wherein the holding member passageway, the base passageway, and the tensioning member passageway are coaxial.

21. The material processing apparatus of claim 1, wherein the inner member defines an inner member shoulder; and
   wherein the tensioning member defines a tensioning member shoulder that mates with the inner member shoulder.

\* \* \* \* \*